(12) United States Patent
Tunay

(10) Patent No.: US 7,495,537 B2
(45) Date of Patent: Feb. 24, 2009

(54) METHOD AND APPARATUS FOR DYNAMIC MAGNETIC FIELD CONTROL USING MULTIPLE MAGNETS

(75) Inventor: Ilker Tunay, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 434 days.

(21) Appl. No.: 11/502,335

(22) Filed: Aug. 10, 2006

(65) Prior Publication Data

US 2007/0038410 A1 Feb. 15, 2007

Related U.S. Application Data

(60) Provisional application No. 60/706,990, filed on Aug. 10, 2005.

(51) Int. Cl.
*H01F 7/02* (2006.01)

(52) U.S. Cl. ..................................... 335/306

(58) Field of Classification Search .................. 335/306
See application file for complete search history.

(56) References Cited

U.S. PATENT DOCUMENTS

| | | | |
|---|---|---|---|
| 5,168,231 A * | 12/1992 | Aubert | 324/320 |
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,662,034 B2 | 12/2003 | Segner et al. | |

(Continued)

*Primary Examiner*—Elvin G Enad
*Assistant Examiner*—Alexander Talpalatskiy
(74) *Attorney, Agent, or Firm*—Harness, Dickey & Pierce, P.L.C.

(57) ABSTRACT

A method and apparatus for dynamic magnetic field control using multiple magnets. Control methods and system means are described that allow dynamically changing the magnetic field generated at a point in space by a multiplicity of magnets.

20 Claims, 15 Drawing Sheets

U.S. PATENT DOCUMENTS

| | | | |
|---|---|---|---|
| 6,677,752 | B1 | 1/2004 | Creighton, IV et al. |
| 6,702,804 | B1 | 3/2004 | Ritter et al. |
| 6,733,511 | B2 | 5/2004 | Hall et al. |
| 6,755,816 | B2 | 6/2004 | Ritter et al. |
| 6,817,364 | B2 | 11/2004 | Garibaldi et al. |
| 6,834,201 | B2 | 12/2004 | Gillies et al. |
| 6,902,528 | B1 | 6/2005 | Garibaldi et al. |
| 6,911,026 | B1 | 6/2005 | Hall et al. |
| 6,968,846 | B2 * | 11/2005 | Viswanathan ............... 128/899 |
| 6,975,197 | B2 * | 12/2005 | Creighton, IV ............. 335/306 |
| 6,980,843 | B2 | 12/2005 | Eng et al. |
| 7,008,418 | B2 | 3/2006 | Hall et al. |
| 7,010,338 | B2 | 3/2006 | Ritter et al. |
| 7,019,610 | B2 | 3/2006 | Creighton, IV et al. |
| 7,020,512 | B2 | 3/2006 | Ritter et al. |
| 7,066,924 | B1 | 6/2006 | Garibaldi et al. |
| 2001/0038683 | A1 | 11/2001 | Ritter et al. |
| 2002/0019644 | A1 | 2/2002 | Hastings et al. |
| 2002/0177789 | A1 | 11/2002 | Ferry et al. |
| 2004/0006301 | A1 | 1/2004 | Sell et al. |
| 2004/0019447 | A1 | 1/2004 | Shachar |
| 2004/0064153 | A1 * | 4/2004 | Creighton et al. .............. 607/1 |
| 2004/0068173 | A1 | 4/2004 | Viswanathan |
| 2004/0096511 | A1 | 5/2004 | Harbum et al. |
| 2004/0133130 | A1 | 7/2004 | Ferry et al. |
| 2004/0157082 | A1 | 8/2004 | Ritter et al. |
| 2004/0158972 | A1 | 8/2004 | Creighton, IV et al. |
| 2004/0186376 | A1 | 9/2004 | Hogg et al. |
| 2004/0199074 | A1 | 10/2004 | Ritter et al. |
| 2004/0249262 | A1 | 12/2004 | Werp et al. |
| 2004/0249263 | A1 | 12/2004 | Creighton, IV |
| 2004/0260172 | A1 | 12/2004 | Ritter et al. |
| 2005/0020911 | A1 | 1/2005 | Viswanathan et al. |
| 2005/0043611 | A1 | 2/2005 | Sabo et al. |
| 2005/0065435 | A1 | 3/2005 | Rauch et al. |
| 2005/0096589 | A1 | 5/2005 | Shachar |
| 2005/0113628 | A1 | 5/2005 | Creighton, IV et al. |
| 2005/0113812 | A1 | 5/2005 | Viswanathan et al. |
| 2005/0119687 | A1 | 6/2005 | Dacey, Jr. et al. |
| 2005/0182315 | A1 * | 8/2005 | Ritter et al. .................. 600/411 |
| 2005/0256398 | A1 | 11/2005 | Hastings et al. |
| 2006/0009735 | A1 | 1/2006 | Viswanathan et al. |
| 2006/0025679 | A1 | 2/2006 | Viswanathan et al. |
| 2006/0036125 | A1 | 2/2006 | Viswanathan et al. |
| 2006/0036163 | A1 | 2/2006 | Viswanathan |
| 2006/0041178 | A1 | 2/2006 | Viswanathan et al. |
| 2006/0041179 | A1 | 2/2006 | Viswanathan et al. |
| 2006/0041180 | A1 | 2/2006 | Viswanathan et al. |
| 2006/0041181 | A1 | 2/2006 | Viswanathan et al. |
| 2006/0041245 | A1 | 2/2006 | Ferry et al. |
| 2006/0058646 | A1 | 3/2006 | Viswanathan |
| 2006/0074297 | A1 | 4/2006 | Viswanathan |
| 2006/0079745 | A1 | 4/2006 | Viswanathan |
| 2006/0079812 | A1 | 4/2006 | Viswanathan |
| 2006/0093193 | A1 | 5/2006 | Visawanathan |
| 2006/0094956 | A1 | 5/2006 | Viswanathan |
| 2006/0100505 | A1 | 5/2006 | Viswanathan |
| 2006/0114088 | A1 | 6/2006 | Shachar |
| 2006/0116633 | A1 | 6/2006 | Shachar |
| 2006/0144407 | A1 | 7/2006 | Aliberto et al. |
| 2006/0144408 | A1 | 7/2006 | Ferry |

* cited by examiner

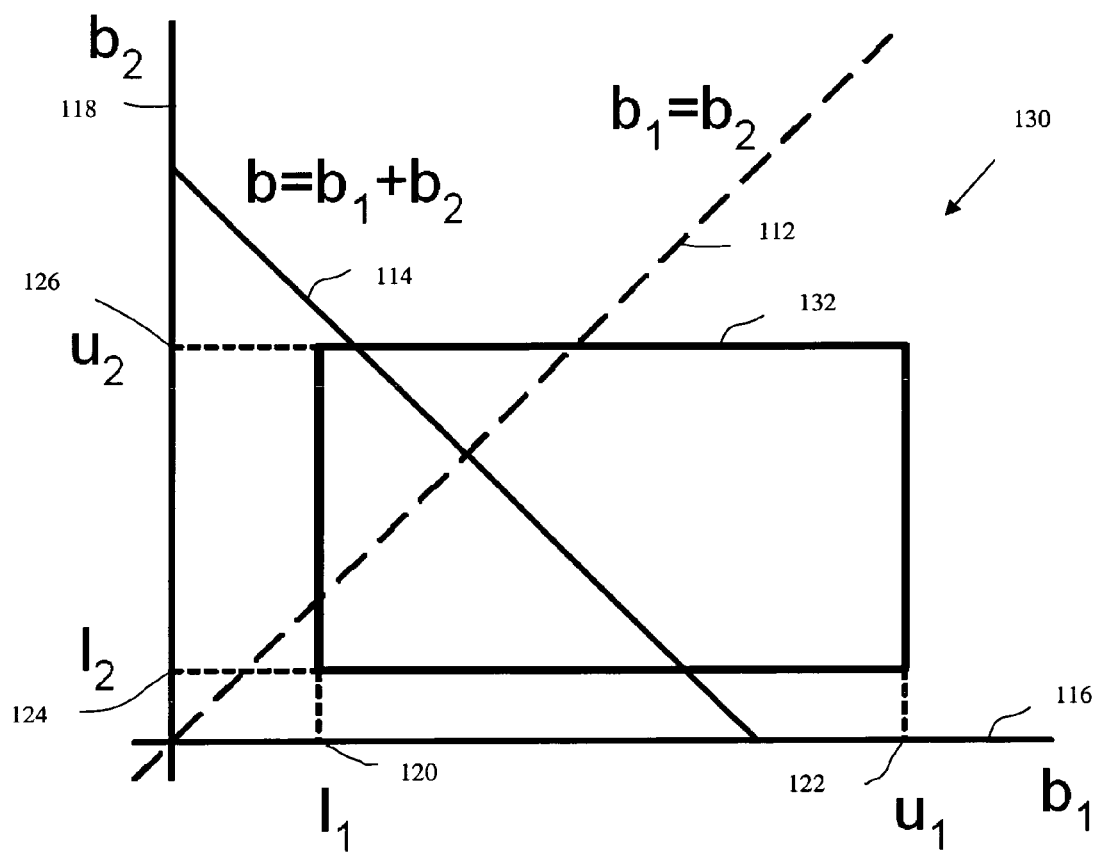
Fig. 9-A

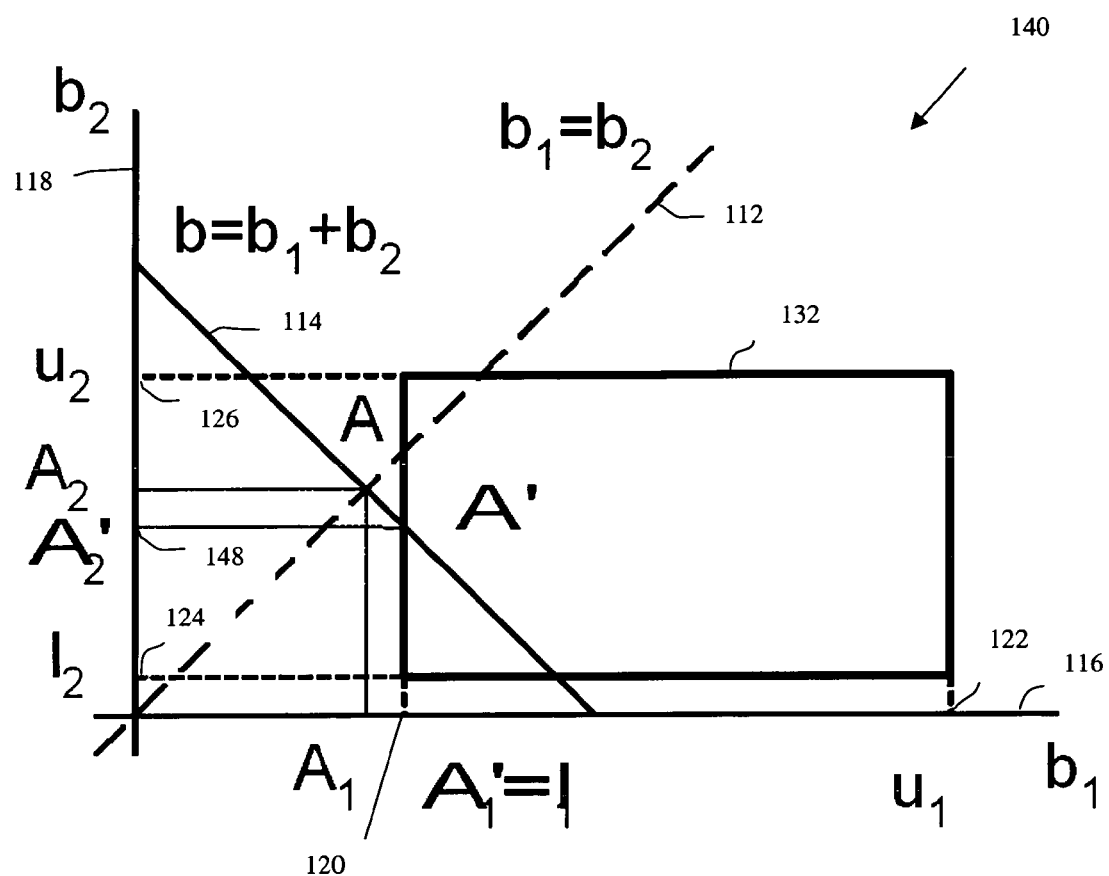
Fig. 9-B

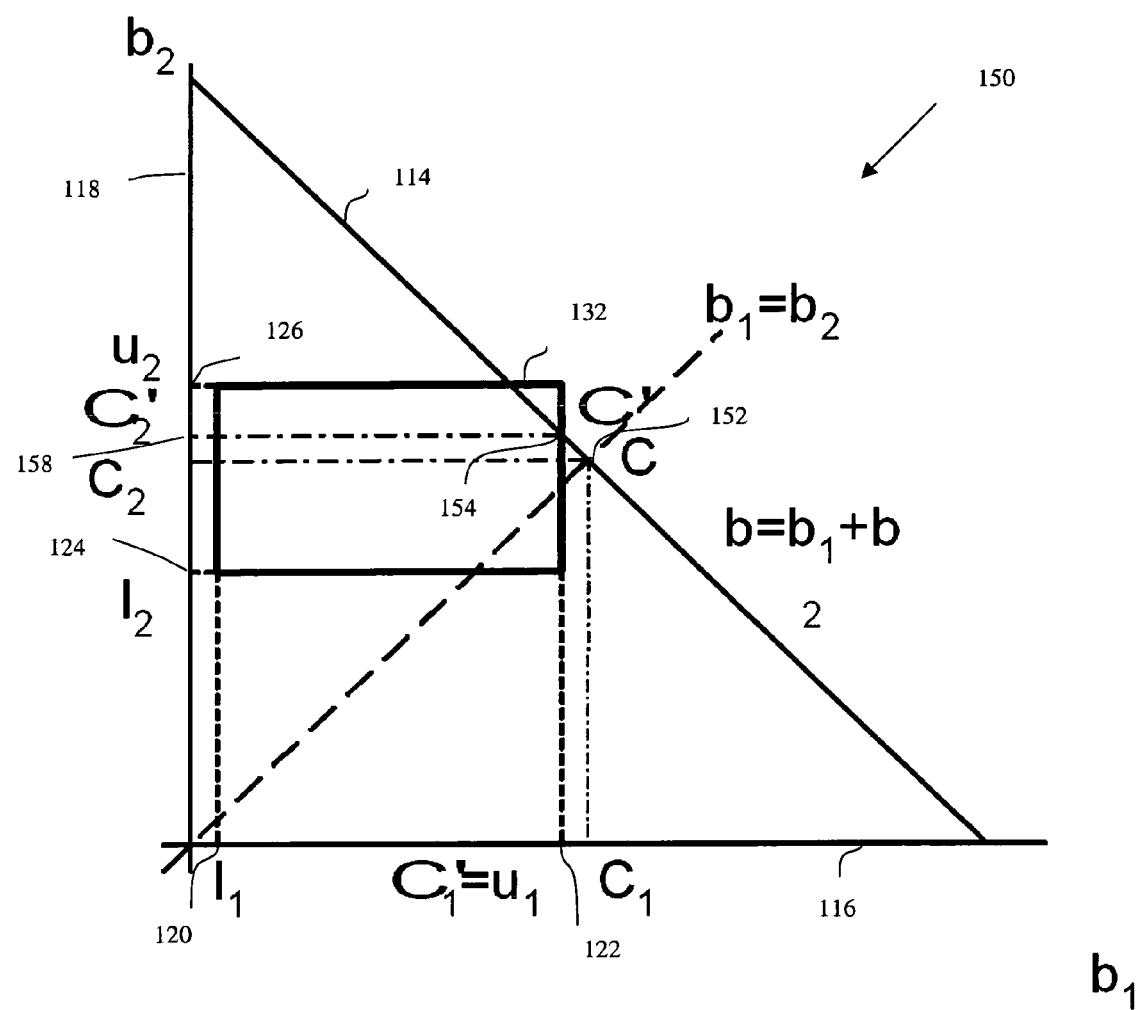
Fig. 9-C

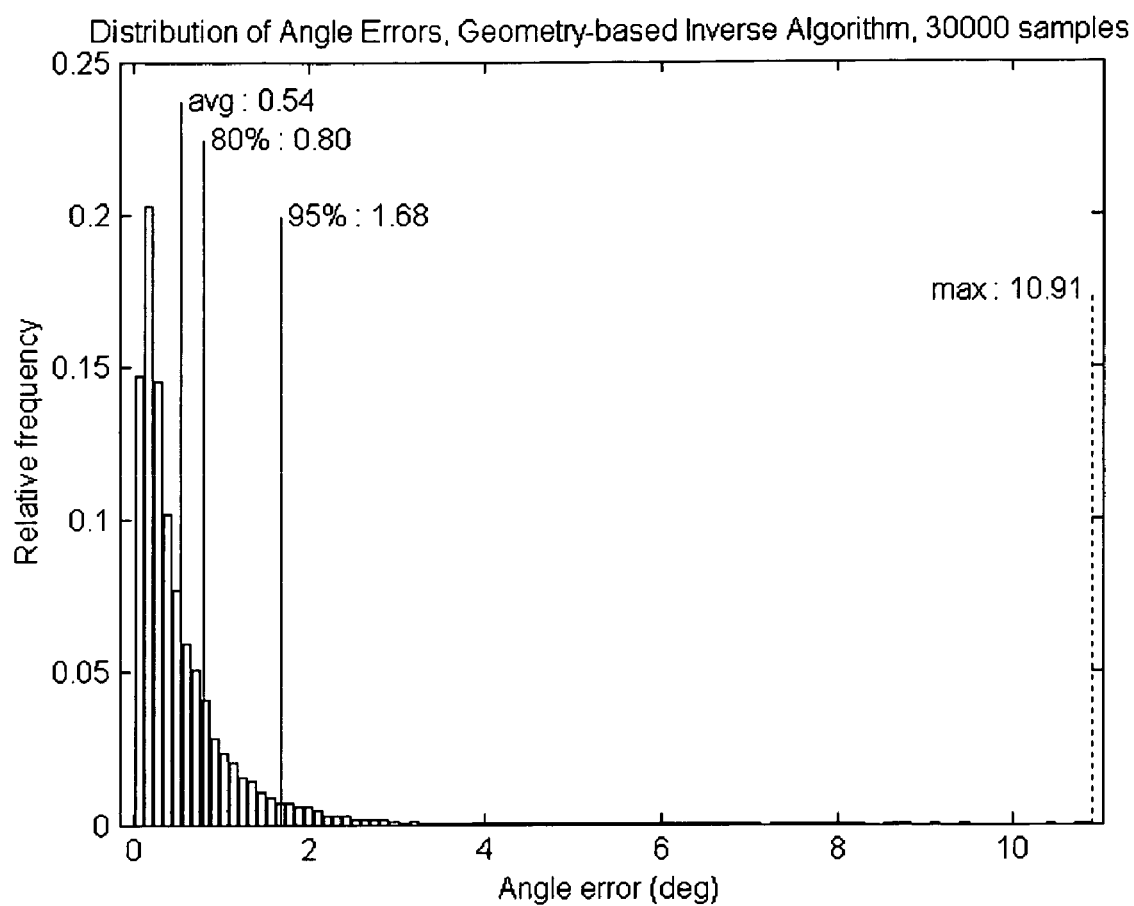
Fig. 10-A

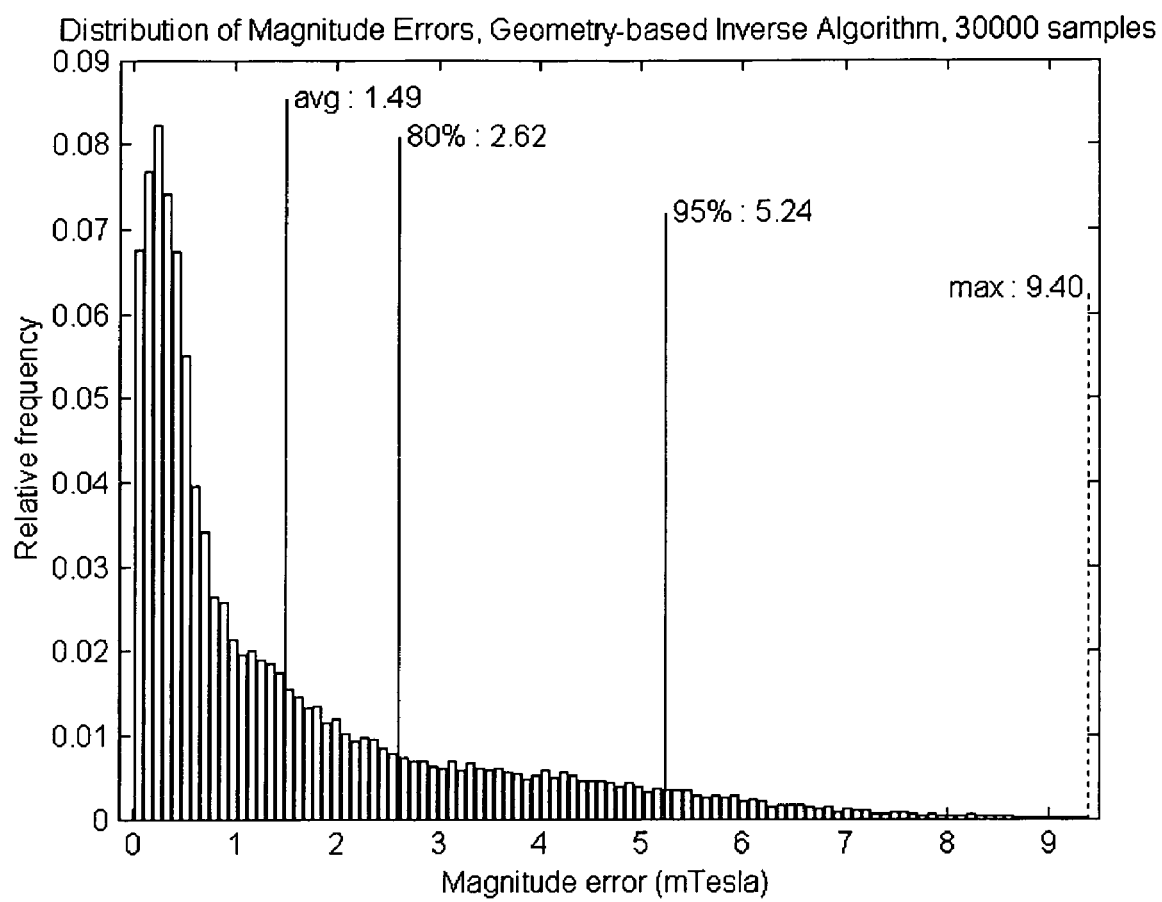
Fig. 10-B

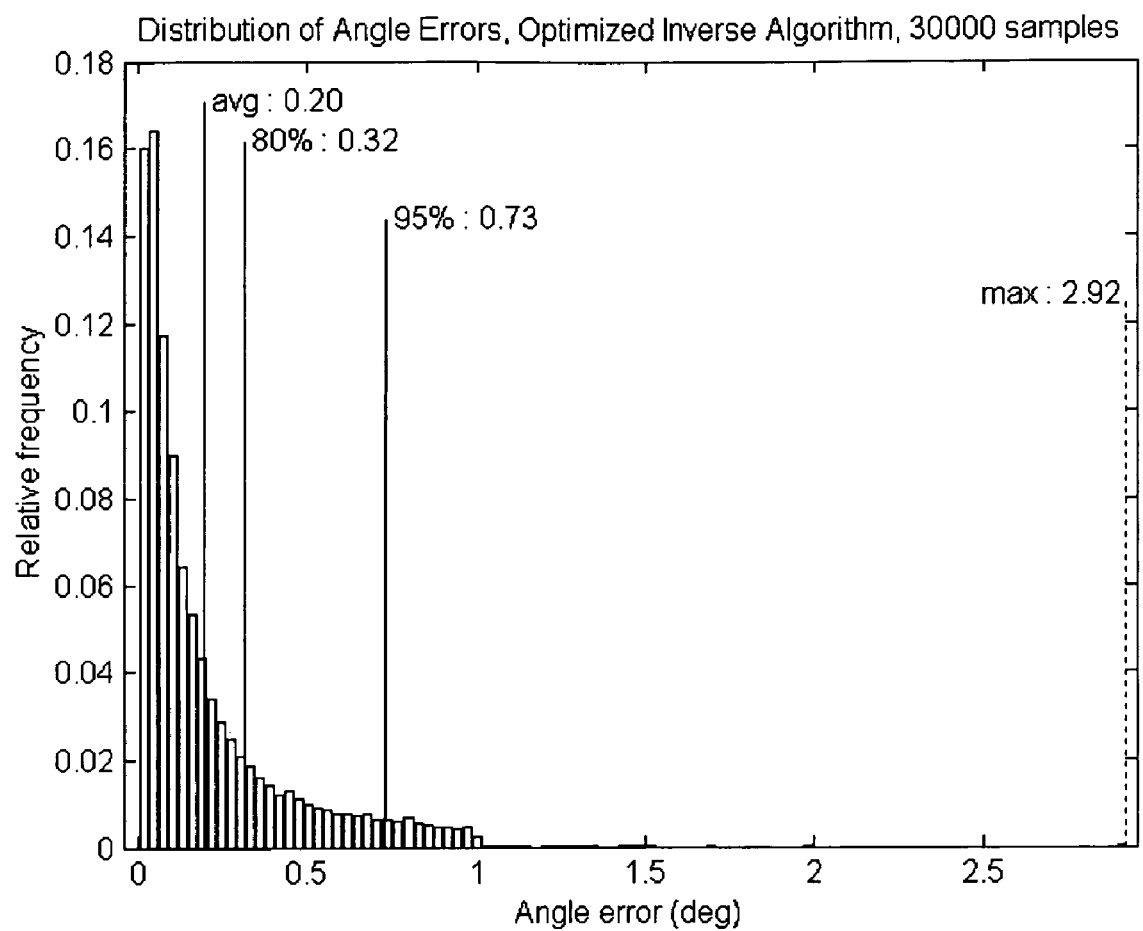
Fig. 11-A

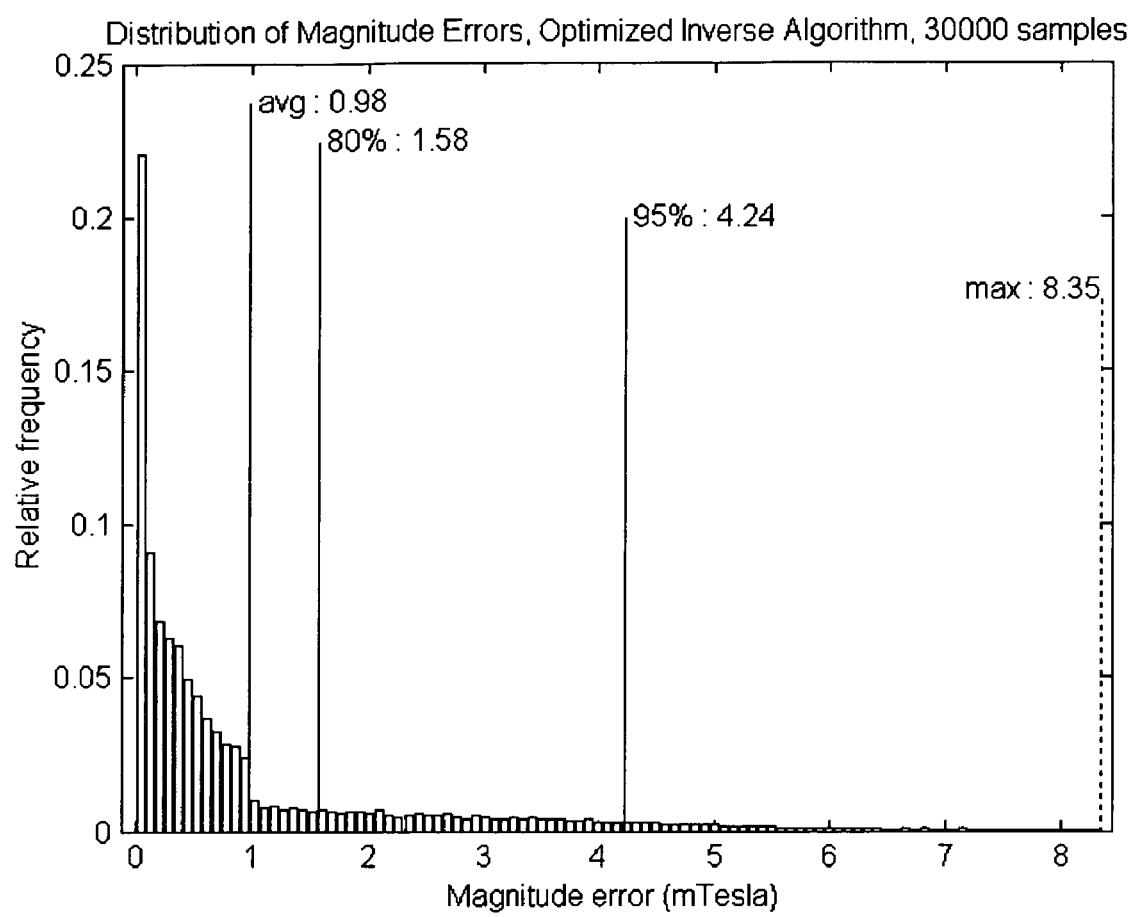
Fig. 11-B

METHOD AND APPARATUS FOR DYNAMIC MAGNETIC FIELD CONTROL USING MULTIPLE MAGNETS

CROSS-REFERENCE TO RELATED APPLICATIONS

This application claims the benefit of U.S. Provisional Patent Application Ser. No. 60/706,990 filed on Aug. 10, 2005, the entire disclosure of which is incorporated herein by reference.

FIELD

This invention relates to the dynamic control of a magnetic field generated by two or more articulated magnets.

BACKGROUND

The robotic control and articulation of objects has been the subject of many investigations. The control of the direction and magnitude of a magnetic field created by a multiplicity of articulated source magnets is a more complex topic that has been studied only more recently. In such a situation, the relatively simple geometric relationships defining transformations between fixed and moving coordinate systems used in ordinary robotics must be supplemented with knowledge of the magnetic fields generated by the source magnets. These fields are typically represented by non-linear functions that most often are not trigonometric in nature. While this problem has been investigated in a few specific cases, no general method has been described that allows automatic control of the magnets to generate a specific magnetic field at a given point in space. Embodiments of the present invention describe a general solution to this problem.

One of the embodiments of the methods disclosed applies to operator-directed control of the magnetic field direction and magnitude generated by two articulated magnets in an operating region. In a specific application, the magnets considered are permanent magnets generally facing one another and the operating region is centered in between the two magnets. The operator-directed control is executed by means of electromechanical positioners that move the two magnets appropriately. The six degrees of freedom (three for each magnet) allow each magnet to translate along the line between the two magnet centers, and each magnet to rotate in two angles $\theta$ and $\phi$ along respective axes. Other similar embodiments that could be used to control a multiplicity of magnets to generate a specific magnetic field (direction and magnitude) at a specific point in space are also included in the present invention.

In magnetic navigation applications, it is desirable to change the orientation (and possibly magnitude) of the magnetic field at the operating point to orient the tip of a catheter or guide wire with respect to the field. The catheter or guide wire is then guided through the subject's vasculature while being simultaneously pushed at the proximal insertion point. It is further desirable to provide a "proper turn" from the initial to the final field vector at the given operating point. A proper turn is a rotation of the magnetic field direction in the plane formed by these two vectors. The concept of a proper turn and its execution is described in U.S. Pat. No. 6,702,804, issued Mar. 9, 2004, from application Ser. No. 09/678,640 filed Oct. 3, 2000, for Method for Safely and Efficiently Navigating Magnetic Devices in the Body, incorporated herein by reference.

SUMMARY

The procedure to execute a proper turn in a preferred embodiment of the present invention entails setting a series of steps for the turn, i.e. finding intermediate field vectors (directions and magnitudes) which couple the two known (initial and target) field vectors at the operating point through the turn.

For each intermediate magnetic field vector the problem of finding the articulations or values of the parameters describing each of the degrees of freedom for the magnets necessary to generate the given field is the inverse problem of finding the field position, direction, and magnitude of magnets having specific articulations.

For each intermediate magnetic field vector at the operating point, and in one embodiment of the present invention, the inverse problem referred to above is solved in three steps. In the first step, the magnitude of the desired field at the operating point is apportioned to the two contributing fields of the two articulated magnets. In the second step, an approximate representation for each magnetic field generated by each magnet is used to ensure quick convergence of the algorithm to an approximate solution. In the third step, optimization methods are applied to a more accurate and mathematically complex field representation to obtain a refined estimate of the magnets control parameters and a more accurate field solution.

In the first step, the magnetic field apportionment algorithm operates under various constraints related to the nature of magnet design and field distributions to optimize field uniformity near the operating point.

In the second step, and in one embodiment of the present invention, a nested polynomial representation for each of the magnet fields enables an efficient solution to the inverse problem. These representations are based on calibration data acquired prior to any navigation procedure. Optimization operates separately for each magnet in consideration of the apportioned fields.

In the third step, and given that the output of the second step is in the neighborhood of the optimal solution, the inverse problem is formulated as a simultaneous optimization in all degrees of freedom, and the approximate polynomial field representation of step two is replaced by a more accurate field representation. One embodiment of the present invention uses a spherical harmonics expansion field representation.

In accordance with one aspect of the present invention, a multiplicity of N magnets ($N>=2$) is controlled to achieve a target magnetic field at a point in space (the operating point). The control algorithm proceeds in three steps. In the first step, the target field is apportioned between the N magnets. In the second step, the inverse problem of finding the magnets articulations that provide the apportioned field at the operating point is solved independently for each of the N magnets using a first level of magnetic field representation. In the third step, the problem of finding the magnet articulations that generate the target field at the operating point is formulated as a simultaneous constrained optimization problem for all N magnets. The third step uses the output of step two as a starting point in the neighborhood of the optimal solution and also uses a more accurate, second level of magnetic field representation for optimization.

The magnets preferably comprise one or more three types: permanent, permanent focusing, or electromagnetic, and are preferably permanent magnets.

BRIEF DESCRIPTION OF THE DRAWINGS

FIG. 9 illustrates for the case N=2 the constraints on each of the two field magnitudes and a method to select apportioned values for the two magnets. FIG. 9-A presents the case when the two magnitudes can be set equal; FIG. 9-B and FIG. 9-C illustrate alternative magnitude apportionment choices when selecting equal magnitudes for the two fields does not lead to a satisfactory solution due to minimum and maximum magnitude constraints on each of the fields.

FIGS. 10-A and 10-B present respectively angle and magnitude error distributions achieved by step 2 of the inverse algorithm, using a nested polynomial representation for each of the fields and independent optimization for each magnet.

FIGS. 11-A and 11-B present respectively corresponding angle and magnitude error distributions achieved by the optimized inverse algorithm of step 3, using a local spherical harmonics function expansion and simultaneous optimization in all variables.

Corresponding reference numerals indicate corresponding parts throughout the several views of the drawings.

DETAILED DESCRIPTION

In one embodiment of the present invention, control of two permanent magnets enables dynamic generation of a specific magnetic field at an operating point. The operating point may be chosen anywhere within a sphere of specific radius centered mid way between the two magnets in their calibration frame positions (at $\theta_i=\phi_i=0$; i=1,2). To relate the magnetic fields generated by each of the two magnets to that present at the operating point, three Cartesian coordinates systems are defined: one associated with each of the two magnets, and a third associated with the subject (world coordinate system). A given vector, such as that representing the desired magnetic field at the operating point within the subject, can be represented in each of these coordinate systems through the usual coordinate transformations. The generation of a dynamic magnetic field at the operating point entails motion of the two magnets with respect to each other and also with respect to the subject. The position of the operating point in each magnet coordinate system will change, as well as the direction of the desired and intermediate field vectors. Accordingly, a series of intermediate magnetic field vectors that lie in a plane in the subject coordinate system will not in general lie in a plane of either of the magnet coordinate systems. The location and orientation of the two magnets at a given time is called the state of the system at that time. The system state evolves in time as necessary to carry out a proper turn.

Figure 1:
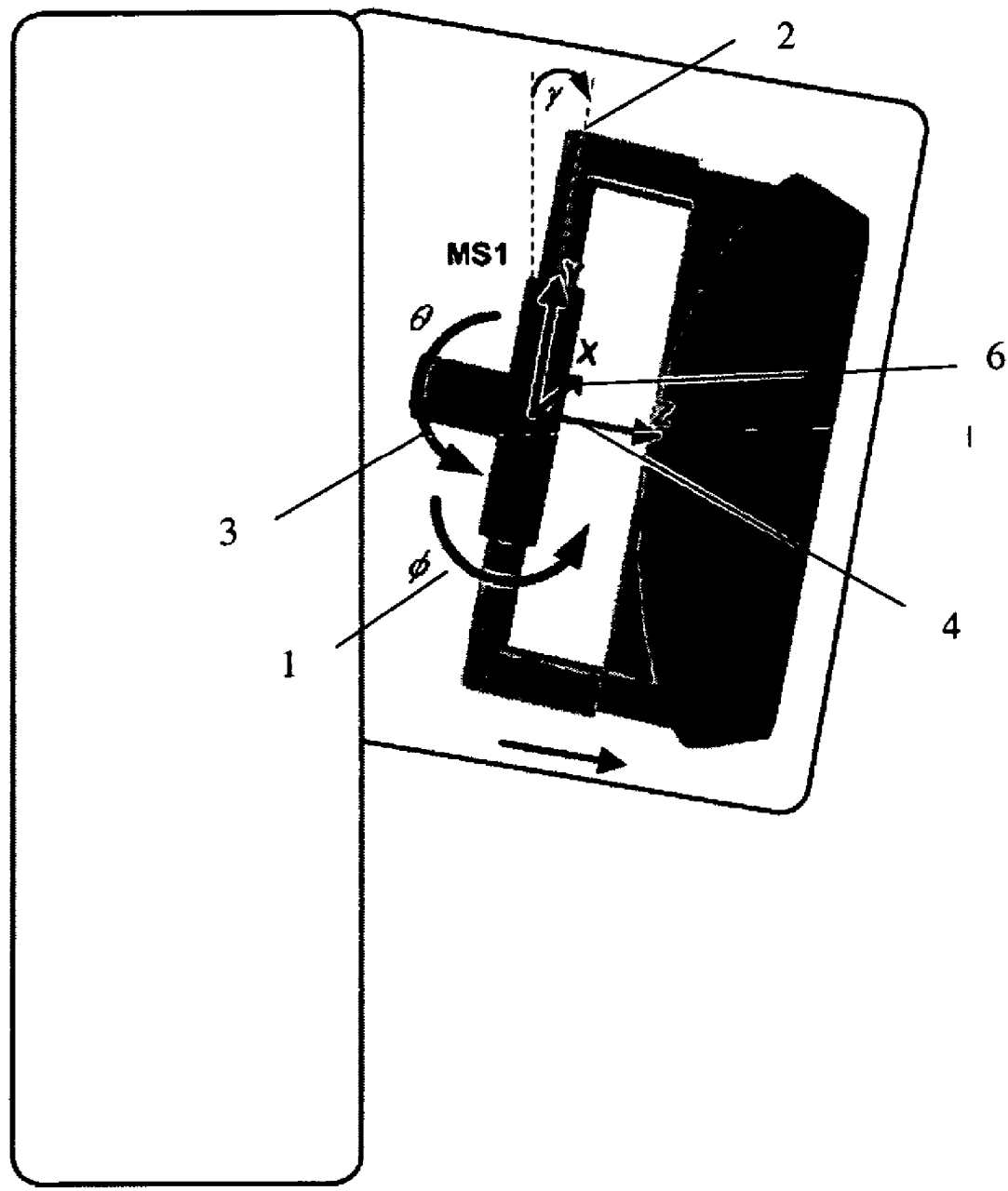
FIG. 1 is a schematic representation of one of the magnets and associated motion axes, including rotation angle θ and pivoting angle φ.
Figure 2:
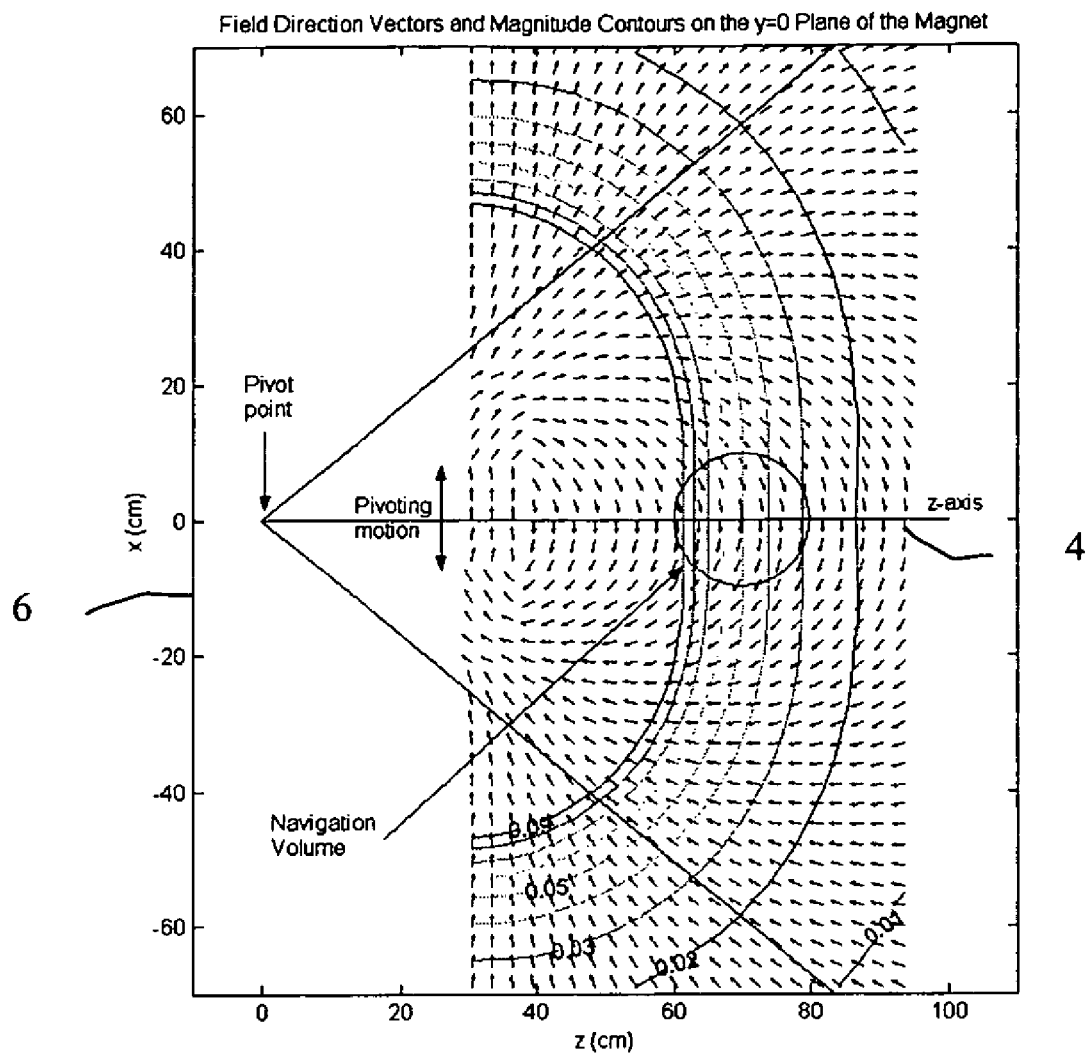
FIG. 2 presents a typical magnet field distribution and associated magnitude contours in the plane $Y^M=0$ (in the coordinate system associated with the magnet).

The Cartesian referential frame ($X^M$, $Y^M$, $Z^M$) associated with each magnet is described in FIG. 1. FIG. 2 illustrates the field distribution in the central ($X^M$, $Z^M$) magnet plane. By design this is a plane of even field symmetry with respect to $Y^M$. Proceeding in the $Y^M$ direction, succeeding ($X^M$, $Z^M$) planes have similar but gradually changing field patterns.

Returning to FIG. 1, and considering one magnet among the multiplicity of magnets under control, two mechanical rotations and a translation defined with respect to the magnet coordinates allow for changing the field distribution in the world (subject) coordinates. These motions are defined as follows:

"Pivoting" in the text refers to a rotation by an angle φ, 1, about the $Y^M$ axis 2. This motion alters the contributions of the X and Z components of this magnet to the field at the operating point.

"Rotation" in the text refers to a rotation by an angle θ, 3, about an axis that coincides with the $Z^M$ axis 4 when the pivot angle is zero; this motion controls the central symmetry plane of the magnet, and is used to align this particular magnet central plane with the target field $B^T$ at the operating point. The effect of this motion is to provide a Y component of the field of this magnet at the operating point.

"Translation" in the text refers to translating the magnet by a distance Z along an axis that coincides with the $Z^M$ axis 4 when the pivot angle is zero; this motion controls the field magnitude.

Functionally, rotation is used to orient the magnet central plane($X^M$, $Z^M$) such that it contains the target field $B^T$. Pivoting adjusts the direction of the magnet axes ($X^M$, $Z^M$) so that axis $-X^M$, 6, is aligned with $B^T$ and the $Z^M$ component of $B^T$ in the magnet central plane is reduced to zero; if that component (the $Z^M$ component of $B^T$) is small to start with then the need for pivoting is reduced, as is desirable from a mechanical stand point.

The following description of the preferred embodiment of the present invention is divided in three parts: A) Field representation; B) Navigation method; and C) Inversion method. In part A), various methods of describing the magnetic fields at several levels of accuracy and complexity are described. Part B) further formulates the problem of magnetic navigation as that of fitting intermediate field vectors that define a proper turn while meeting a number of design constraints. In Part C), for each of the intermediate magnetic field vectors, the inverse problem of finding the magnet articulations that generate such a magnetic field at the operating point is solved in three steps. The first step apportions the total magnetic field magnitude to each of the magnets. Step two finds an approximate solution by solving the inverse problem for each of the magnets independently, given the first level of magnetic field representation introduced above and the apportioned fields of step one. Step three finds an improved solution by simultaneously solving the problem for all magnets and using a more accurate field representation.

Part A): Field Representation

The magnet design is meant to generate a specific magnetic field in a three dimensional volume. Independently of the magnet design specifications, the generated fields can be represented to any level of accuracy by a finite element model or by three dimensional look-up tables. Such representations are inefficient in that they require storage of a large amount of data (in function of the desired accuracy) and lead to the use of computationally intensive three-dimensional interpolation methods. In one embodiment of this invention, the magnetic fields requirements are specific to magnetic navigation of catheters and guide wires in the body of a subject. In this embodiment, the actual fields generated by magnets designed per the corresponding specifications can be approximated to a very good accuracy by a basis expansion on spherical harmonic functions using a finite number of terms. In this representation, and referring to FIG. 1, the even and odd symmetries of specific field components with respect to the magnet's $Y^M$ and $Z^M$ axes 2 and 4 are taken into account. Commonly, the expansion coefficients are determined through a calibration procedure using the field values on an imaginary sphere containing the magnet. In particular, such a representation can satisfy the Laplace equation that applies to stationary magnetic fields, and can also be used to locally represent the field in a specific volume (such as within a sphere enclosing the operating point) to a very high degree of accuracy.

However, such an expansion on spherical harmonics functions may not be the most efficient means to represent the field distribution within a given accuracy and a limited number of coefficients. Further, such a representation might not be optimal in terms of performing the inverse calculations that are necessary to determine the system state that will generate a specific field at the operating point. In one embodiment of the present invention, these two limitations are addressed by defining two levels of field representation. The first level of accuracy uses nested polynomials to provide a simplified field representation that allows efficient inversion algorithm convergence for each magnet independently to a state vector in the neighborhood of the optimum. In the second level of field representation accuracy, the coefficients of the spherical harmonics expansion are calculated by performing a least squares minimization between the representation and the actual field in a specified volume of interest. The volume of interest can be defined by a sphere that will encompass the operating point under all practical magnetic navigation situations. Such a local representation allows both a minimized error within the volume of interest for a given number of expansion terms as well as improved convergence of the inversion algorithm.

Figure 3:
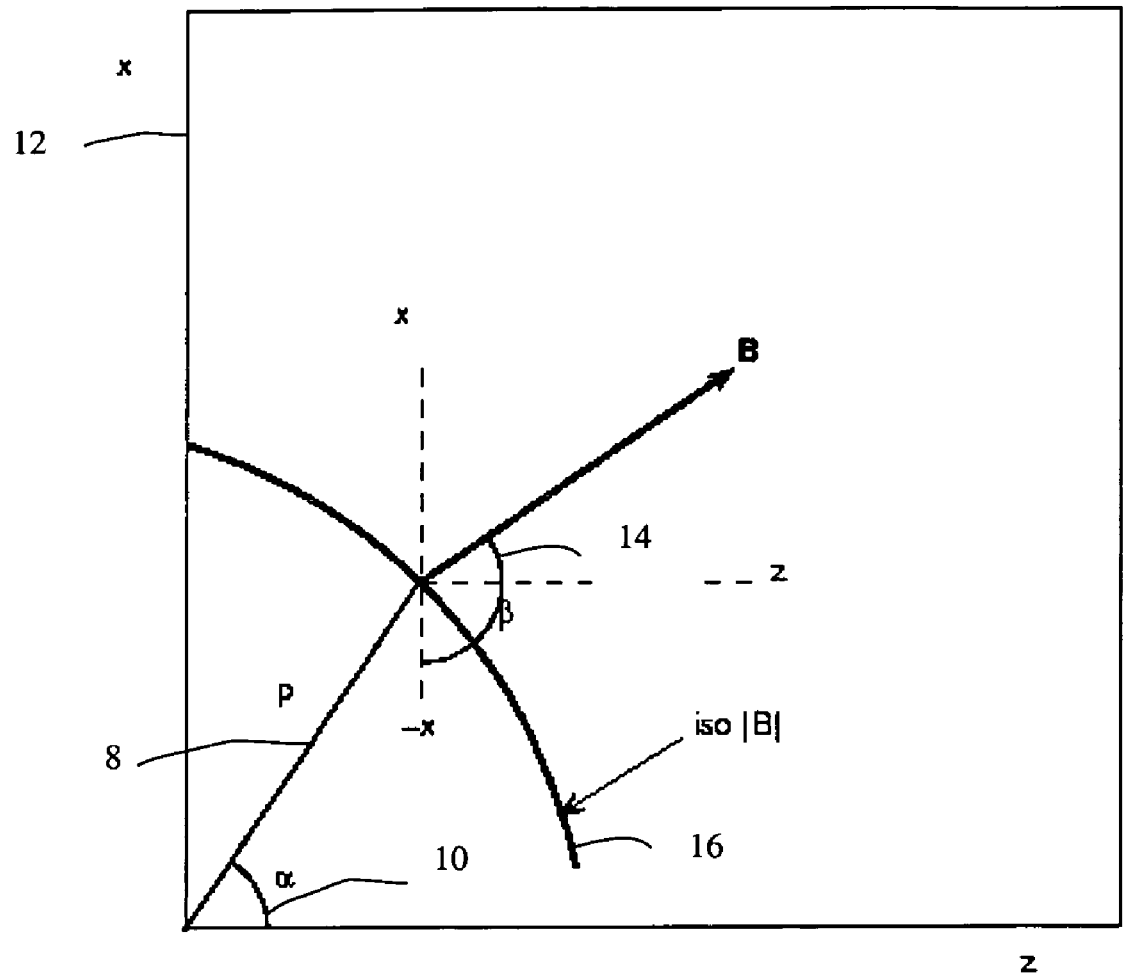
FIG. 3 shows the parameterization (ρ, α, β) for the orientation and magnitude of the projection of the magnetic field B onto a given ($X^M$, $Z^M$) plane.

For a given magnet, on the central, symmetry plane ($X^M$, $Z^M$), the $Y^M$ component of the magnetic field is small (nominally zero by design). Because the field direction and magnitude vary slowly with distance e from the central plane, and because in a typical navigation configuration the $Y^M$ field components of the two facing magnets tend to combine destructively (the respective $Y^M$ axes being coaxial but in opposite directions), in a first approximation it is natural ignore the $Y^M$ field components. Any actual state vector optimization result obtained under this assumption for a target field within the navigation volume will include a small $Y^M$ field resultant. Under this assumption, the field for each magnet at any point within a volume of interest can then be represented by its orientation in the associated ($X^M$, $Y^M$) plane and magnitude. Referring to FIG. 3, and introducing cylindrical coordinates ($\rho$, $\alpha$, $\gamma$), $\rho$ radial distance 8, $\alpha$ radial angle 10 with respect to axis $Z^M$ 12, and $\gamma$ elevation, the field at any point in the magnet navigation volume is uniquely determined by the knowledge of the angle $\beta=\beta(\rho,\alpha,\gamma)$ 14 and field magnitude $|B|=|B(\rho,\alpha,\gamma)|$. A convenient representation for $\beta$ and $|B|$ uses nested polynomials as described below.

This section details the field magnitude representation. The Bio-Savart law calls for the field magnitude created by an elemental electrical circuit to vary according to the inverse of the square of the distance. It suggests representing the inverse of a macroscopic magnet field magnitude by a polynomial function of distance $\rho$ of limited degree. As inversion of the problem is a necessary step of the method, it is desirable to limit the polynomial order to two; such a representation is also sufficiently accurate for the object of the method. Accordingly, the field magnitude on any point of an iso-$|B|$ curve 16 of FIG. 3 is modeled by:

$$\frac{1}{|B|} = a(\alpha) + b(\alpha)\rho + c(\alpha)\rho^2.$$

In a given ($X^M$, $Z^M$) plane, the field Z-component presents an odd symmetry with respect to axis $Z^M$, and the variations along $\alpha$ for the coefficients a, b, and c can be efficiently represented by a fourth-degree polynomial in $\alpha$:

$$a(\alpha)=a_0+a_1\alpha+a_2\alpha^2+\ldots+a_4\alpha^4$$

$$b(\alpha)=b_0+b_1\alpha+b_2\alpha^2+\ldots+b_4\alpha^4$$

$$c(\alpha)=c_0+c_1\alpha+c_2\alpha^2+\ldots+c_4\alpha^4$$

As indicated above, the field variations along $Y^M$ are relatively slow, and accordingly each of the 15 coefficients $a_0, \ldots, a_4, b_0, \ldots, b_4, c_0, \ldots, c_4$ may in turn be represented by a fourth-degree polynomial function of $Y^M$. The resulting set of 75 coefficients accurately describes the field magnitude at any point in a volume that encompasses the navigation sphere.

This section details the field angle representation. Given the magnitude representation $|B|=|B(\rho,\alpha,\gamma)|$ which for fixed $\alpha$ and $\gamma$ is a one-to-one function of the distance $\rho$, the field angle $\beta^M$ 14 can be represented by a function of $|B|$ and $\alpha$. That is, on a line 16 of constant $|B|$, the field angle $\beta^M$, defined as the angle between the projection of the field vector onto the plane at $Y^M$=constant and the negative X axis of the ($X^M$, $Y^M$) frame, is given by:

$$\beta^M=f(|B|,\alpha).$$

As will be further described below, the control algorithm considers an operating point located on the $Z^M$ axis. For a given apportioned target field $B^T$ at the operating point, the projection of $B^T$ onto ($X^M$, $Z^M$) forms an angle $\beta^T$, $0 \leq \beta^T \leq \pi$, with respect to the $-X^M$ axis. The inverse algorithm then finds the angle $\alpha^T$ such that $\beta^M=f(|B|,\alpha^T)=\beta^T-\alpha^T$. As FIG. 2 shows, $\beta(0)\approx 0$ and $\beta$ grows monotonically from $\beta(-\pi/2)\approx-\pi$ to $\beta(\pi/2)\approx\pi$ and therefore the function $\beta(\alpha)$ is monotonic and one-to-one over the interval $[-\pi/2,\pi/2]$ and such an angle can always be found. Consequently, after pivoting the magnet by an angle $\alpha=\alpha^T$, the magnet field angle, $\beta'=\beta^M+\alpha^T$ (calculated with respect to the fixed world $-X$ axis) will be equal to the target angle $\beta^T$. To simplify the calculations during navigation and application of the algorithm, it is therefore desirable to represent the function $\alpha(\beta)$ inverse of the one-to-one function $\beta^M=f(|B|,\alpha)$. With $\alpha(0)=0$ a cubic polynomial fit can be written as:

$$\alpha=d(|B|)\beta+e(|B|)\beta^3.$$

The coefficients d and e can be modeled as quadratic functions of the field magnitude:

$$d(|B|)=d_0+d_1|B|+d_2|B|^2$$

$$e(|B|) = e_0 + e_1|B| + e_2|B|^2$$

Each coefficient $d_0$, $d_1$, $d_2$, $e_0$, $e_1$, $e_2$, is then modeled as a cubic function of $Y^M$. Accordingly these 24 coefficients provide an accurate representation of the angle $\alpha(\beta)$.

These nested polynomial field representations for field magnitude and angle yield maximum errors of:

$\epsilon(|B|) \leq 1.5$ mTesla, and $\epsilon(\beta) \leq 0.7$ degrees for the range of variables relevant for navigation in the subject volume.

Part B): Navigation Method

The navigation algorithm solves the problem of finding a time sequence of source magnets states such that the final sequence state provides an accurate and precise estimate of the target magnetic field at the operating point. As described above, the state of the system is completely determined given the two magnet $Z_i$ translation coordinates, rotation angles $\theta_i$, and pivoting angles $\phi_i$ (i=1,2). The problem can be more formally stated as:

Given:
an operating point at r, and
$x_0$ (an initial system state) corresponding to an initial field $B_0$ at the operating point, and
$B^T$, the target field at the operating point,
Find x(t) the state evolution to obtain the target field at the operating point.

It is desired that the magnetic field changes in a plane in the subject frame as the system evolves from the initial state $x_0 = x(t_0)$ to the final state $x(t_f)$. In a normal navigation procedure it is also desirable to keep the field magnitude essentially constant; in a well designed magnet system the relative field magnitude variation between initial and final states is not expected to be larger than a few percents.

Constraints are imposed on the velocity and acceleration to which each magnet may be subjected. Z translation constraints are imposed by the fixed magnet covers and other design considerations; also the magnet pivoting angle is limited to a specific range. Mathematically, the procedure to find the desired progression of state x(t) is then:

Minimize the departure of B(t) from the plane formed by $B_0$, $B^T$;

Minimize the difference between the field magnitude |B(t)| and a functional of the initial and final magnitudes $|B_0|$ and $|B^T|$ (such as average of $|B_0|$ and $|B^T|$ or a polynomial fit), Subject to:
$B_f = B(t_f) = B^T$
$Z < Z_n$ ($Z_n$ is the closest position to the system cover)
$-40° < \phi < 40°$
$a_{min} < a < a_{max}$, for all variables Z, $\theta$, $\phi$ (acceleration conditions)
$v_{min} < v < v_{max}$, for all variables Z, $\theta$, $\phi$ (intermediate velocity conditions)
$v_0 = v_f = 0$
$x_0 = x(t_0)$
$x_f = x(t_f)$.

Figure 4:
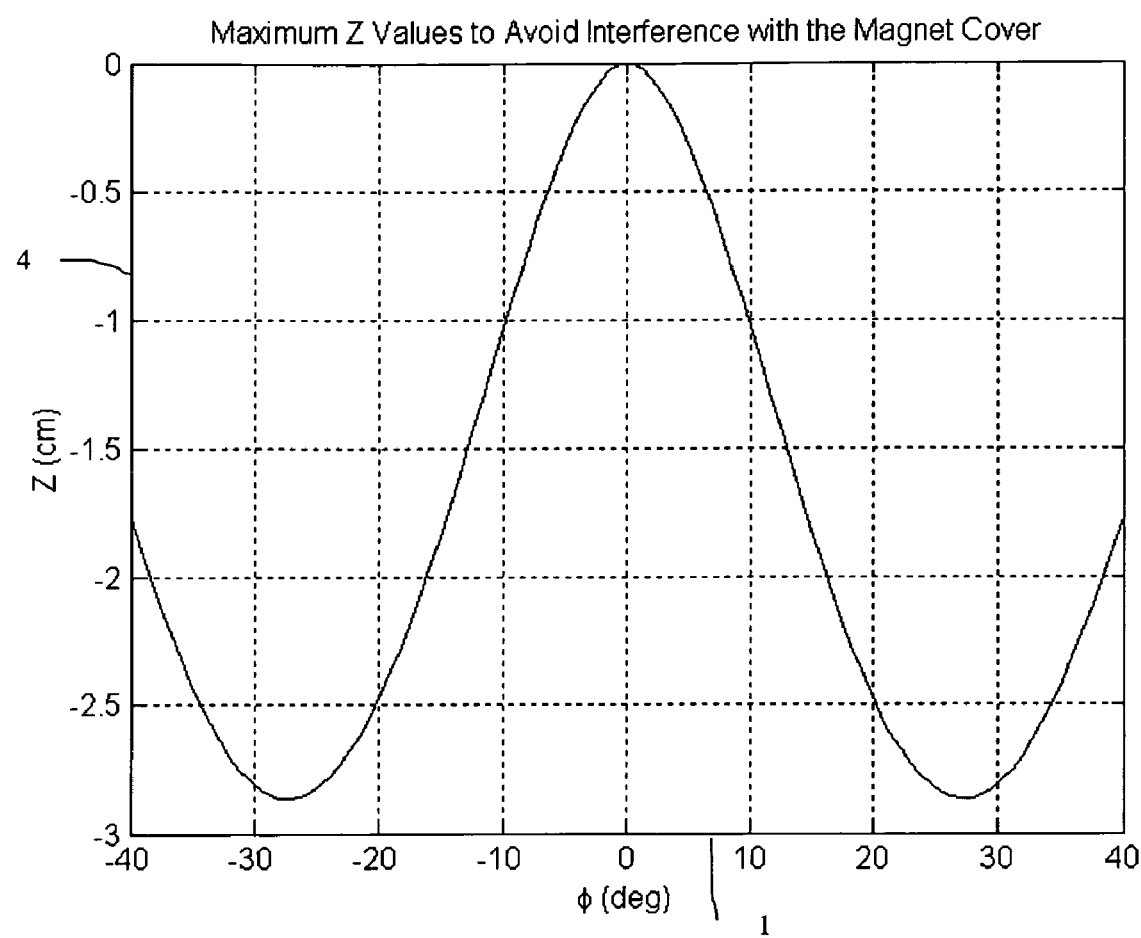
FIG. 4 shows maximum Z values achievable as a function of the pivoting angle φ. This represents the spatial constraint imposed by the fixed magnet covers.

Additional requirements are imposed on the control method. It is often desired in a magnetic medical procedure that the resultant field magnitude at the operating point be kept essentially constant; as for each magnet the contributed field magnitude varies with distance from the magnet center, this is accomplished by translating the magnets to alleviate the field magnitude changes that are unavoidably associated with magnet reorientation (rotation and pivoting). In the preferred embodiment of a magnetic navigation system fixed and close-fitting covers enclose each of the magnets to ensure safety and subject access; the associated limits on magnet translation are magnet orientation-dependent, as illustrated in FIG. 4. The maximum Z value along axis 4 is shown as a function of the pivoting angle $\phi$, 1. In certain orientations the magnet must be pulled back a small distance to avoid collision with the cover. A number of other conditions are imposed to make the motions and articulations more efficient and safe; as examples, it is desirable to limit both the accelerations to which the magnets are subject as well as the resulting velocities; mechanical considerations indicate that it is also desirable to reduce the pivoting motion (angle $\phi$ in FIG. 1). Generally it is favorable to apportion the field magnitudes equally between the two magnets as this field distribution locally minimized field gradients. Yet other conditions and constraints will be shown to be useful in the control method and algorithms that enable performing a proper turn.

A large number of inversion and optimization approaches are described in the literature. Linear problems formulated as least-squares estimation can be solved using matrix approaches. Such problems are written as:

$$\text{Min} \|Ax - b\|^2$$

Degenerate inversion problems (that is, problems with an infinite number of solutions) can be regularized by including a weighted penalty term in the cost function; the additive combination of a degenerate and a non-degenerate quadratic being non-degenerate.

Non-linear constrained optimization problems have been investigated in a number of settings. For a problem formulated as:

$$\text{Min } f(x)$$

$$s.t. \ g_i(x) \leq 0, i \in I$$

a general formalism leading to practical solutions uses a Lagrangian function:

$$L(x, \lambda) = f(x) + \sum_{i \in I} \lambda_i g_i(x)$$

Necessary conditions for local optimum have been given by Kuhn and Tucker. These conditions have also been extended to non-linear problems with both equality and non-equality constraints. It is also clear from the formalism above that a linear problem, such as that of fitting a polynomial to a series of data point, under specific equality and inequality constraints, can be represented and solved through the Lagrangian formalism.

Figure 5:
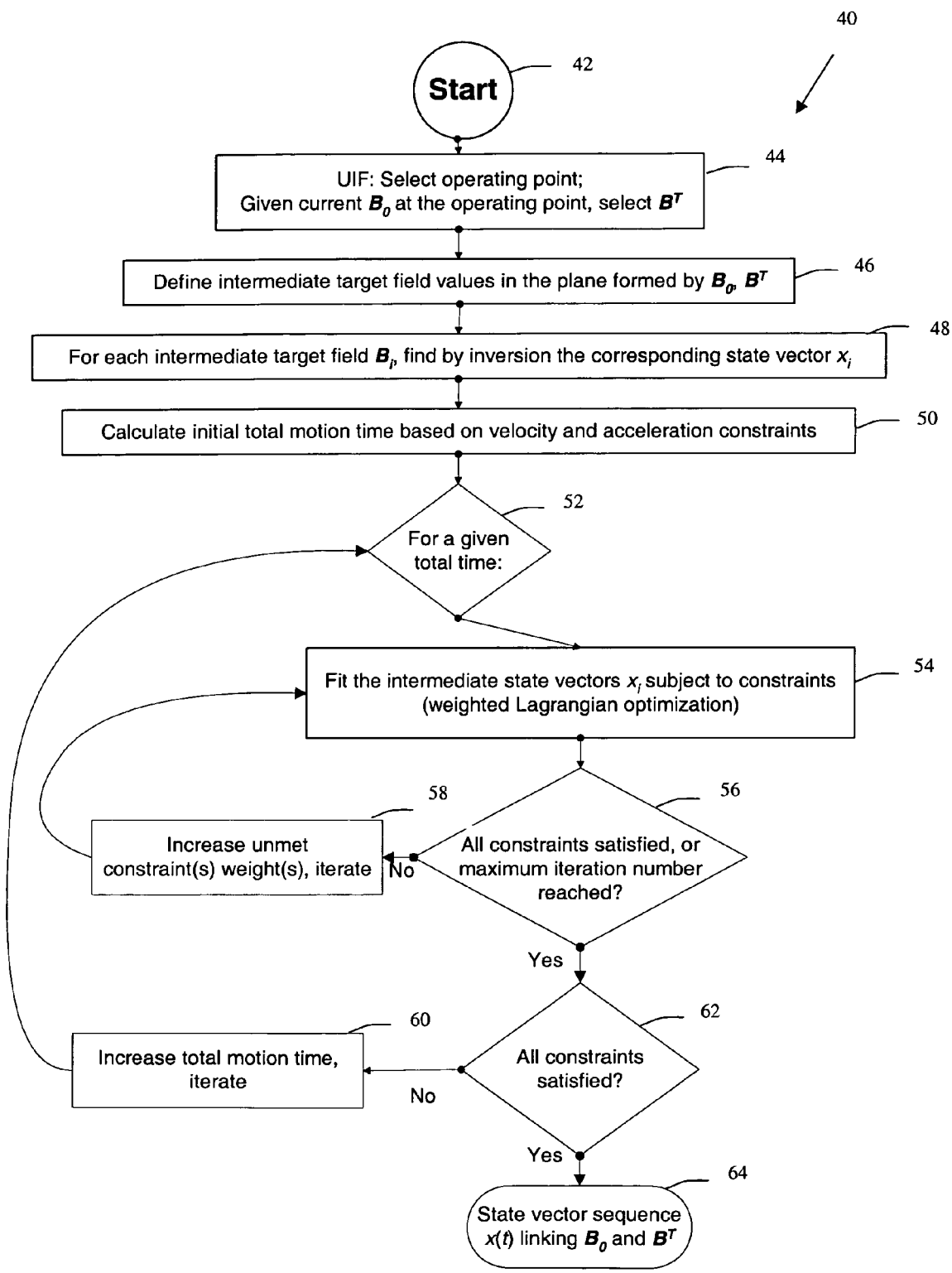
FIG. 5 presents the navigation algorithm flowchart.

The navigation algorithm proceeds in the following five steps, described in more details below, and illustrated in the flowchart 40 of FIG. 5. Given $B_0$, $B^T$, 44:

1. Define intermediate target field values at predetermined angles, 46;
2. For each intermediate field value, calculate by inversion the associated state vectors (these intermediate states will then be fitted), 48;
3. Assess the intermediate interval times based on velocity and acceleration constraints, and determine an initial total time, 50;
4. For a given total time 52, iterate on the following till all the inequality constraints are met or an upper bound on the number of iteration is reached:

5. For the four end constraints (initial and end state and velocity constraints) and additional weighted cost functions (as necessary to represent specific navigation constraints), solve the optimization problem using a Lagrangian approach 54. If, 56, one or more of the inequality constraint(s) is not met, increase the weight on the corresponding constraint, 58, and iterate. If the maximum number of iteration has been met, 60, increase the total time allotted to the motion and iterate. The final state vector sequence 64 is given at the completion of the iteration.

For each magnet and for each of the magnet coordinates Z, θ, φ, the requirements described above translate into four equality constraints (two for the initial and end velocities, and two for the beginning and end state conditions). The inequality requirements translate into additional constraints (four to six depending on the variable). It is possible to design exact methods that will achieve a proper turn by ensuring that intermediate field values lie exactly in the plane formed by the initial and end field vectors. However such methods are computationally expensive and are subject to oscillations (as attempt at polynomial interpolation will demonstrate). A more efficient method consists of specifying intermediate field values (themselves prescribing a proper turn), calculating by inversion the corresponding state values, and fitting these values by a functional. The inversion procedure gives the intermediate state values to be fitted, rather than interpolated, by a polynomial. As there are four equality constraints, and additional inequality constraints, a polynomial of at least degree six is prescribed. At least seven fit nodes or intermediate magnetic field values are used in this embodiment to keep the field close to that of a proper turn.

Figure 6:
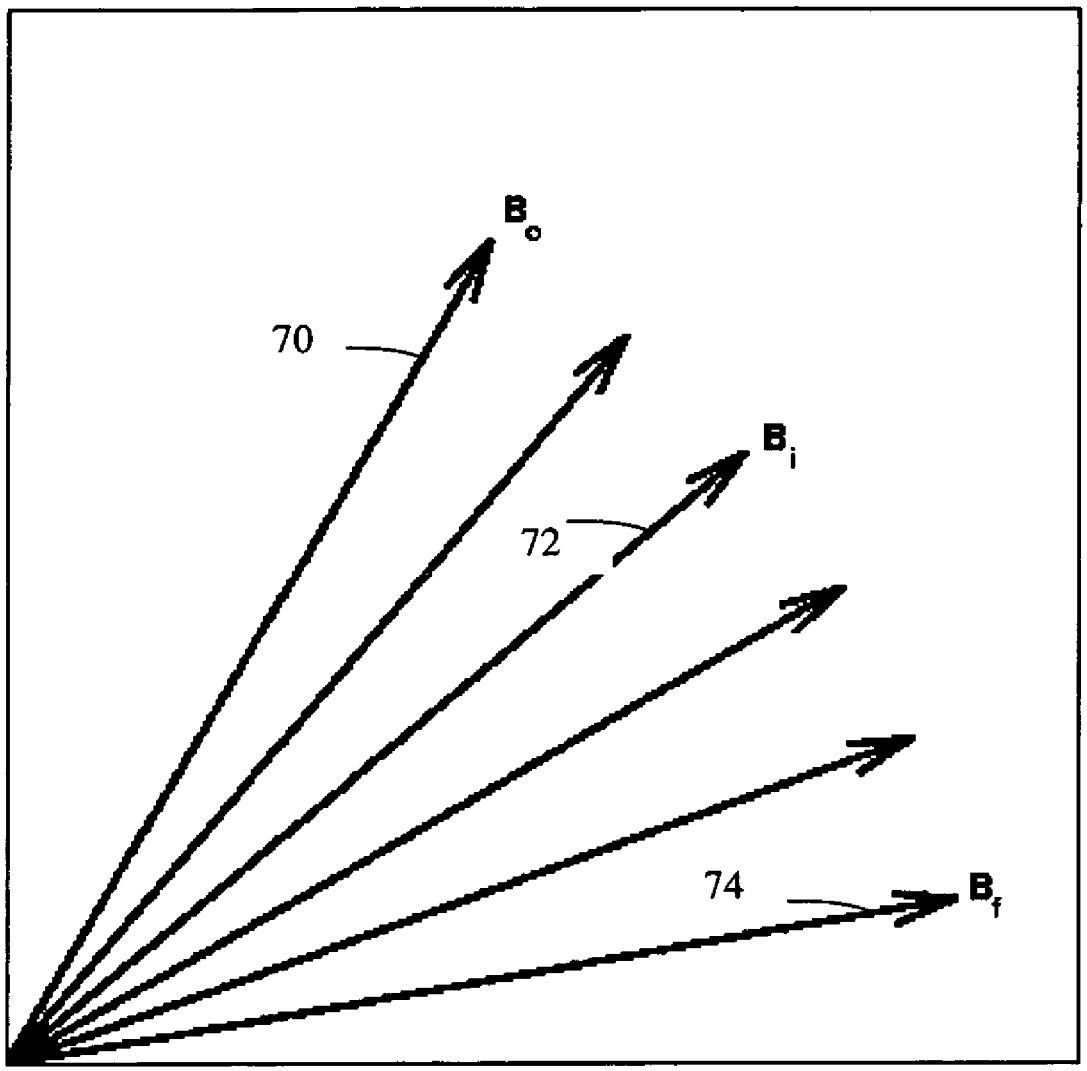
FIG. 6 illustrates the magnetic field vector progression from its initial state $B_0$ to its target state $B^T$ at the operating point through a succession of intermediate field values.

FIG. 6 shows schematically for a navigation turn the intermediate nodes to be fitted during navigation from an initial field $B_0$ 70 to a final field $B^T$ 74 at the operating point 76. The intermediate field values $B_i$, 72, are provided in 10-degrees increments.

The algorithm begins by solving the inverse problem for each intermediate field value $B_i$. The inverse algorithm, described below in Part C), provides the intermediate state vector values to be approximated during navigation through the fitting procedure. Next, the total time $T_f$ for the motion is estimated as follows. For each axis and for each segment joining two adjacent state values the absolute coordinate increment is calculated, and the total distance between initial and final state vector coordinates is then estimated as the sum of the absolute (linear) increments over all segments. Assuming parabolic velocity profiles and using velocity and acceleration constraints, and based on the total distances just calculated, the travel time needed for each axis is calculated. The maximum of all the total axes motion times (plus a small extra amount) gives the total initial motion time $T_f$. To find the intermediate times ti, the times needed for each axis to go from one intermediate position to the next with its maximum velocity are determined. The time needed by the slowest axis in each interval is retained, and all the intermediate times are scaled so that their sum equals the total motion time $T_f$.

Figure 7:
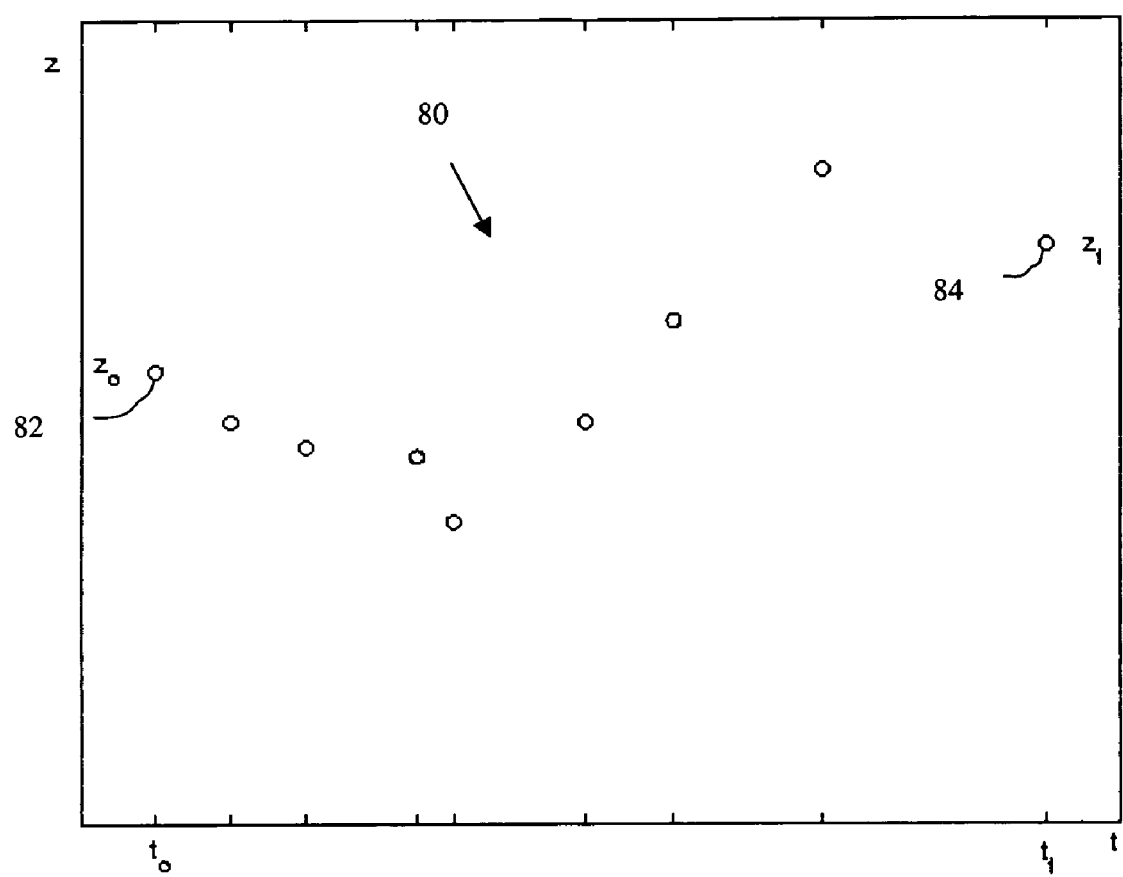
FIG. 7 shows the time progression of one of the state vector elements, Z, through a series of intermediate discrete values.

An illustration of the resulting steps in magnet translation coordinate $Z_i$ for this procedure is shown in FIG. 7. The time series 80 of Z values from $Z_0$ 82 to $Z_f$ 84 for one magnet shows some fluctuation that are to be expected. The polynomial fitting of these points is part of the polynomial method associated with this one of the six magnet coordinates. Comparable figures would show the progression of steps in θ and φ for each of the two magnets. A sixth degree polynomial suitably fits the data. For Z(t) the time progression is modeled as (for the specific basis function retained):

$$Z(t)=y_0+y_1 t+\ldots+y_6 t^6$$

and similar equations are written for the variables θ(t), φ(t), for both magnets. It is noted that the $t_i$ values are not necessarily equally spaced. Solution for the polynomial coefficient can be carried out by means of the associated Vandermonde matrix (p=6):

$$\begin{pmatrix} 1 & 1 & . & 1 \\ t_1 & t_2 & . & t_n \\ . & . & . & . \\ t_1^p & t_2^p & . & t_n^p \end{pmatrix}$$

Other basis function choices would lead to other matrix forms. It is desirable to scale the time values to a limited interval to increase numerical stability. This can be done, for example, by normalizing the time sample values by use of the series distribution mean m, and standard deviation $\sigma_t$: $t_i=(t_i-m_t)/\sigma_t$.

The optimization in terms of the y coefficients that fit the $Z(t_i)$ values must be made subject to the four end point constraint in x and v. A suitable cost function will need four components with relative weights chosen as follows:
1) Fit errors-largest weight;
2) Acceleration root-mean-square-second largest weight;
3) Z and φ root-mean-square distance from center of range of motion-third largest weight;

$$\sum_i y_i^2 - \text{smallest weight}$$

(Vandermonde inversion regularization).

The problem is then solved analytically for the $y_i$ coefficients by minimizing the cost functions subject to the four end point constraints $v_0=v_f=0$, $x_0=x(t_0)$, $x_f=x(t_f)$. This is solved by using a Lagrangian function L, setting $\partial L/\partial x$ and $\partial L/\partial \lambda$ to 0 and finding the corresponding Lagrange multipliers $\lambda_j$.

This procedure provides an initial set of fit coefficient values $y_0, y_1, \ldots, y_6$ for which the end point constraints have been satisfied. The next algorithm step tests whether the inequality constraints are also satisfied. If not, the algorithm increases the weight on the corresponding constraint(s). This procedure is iterated until all constraints are satisfied. Finally, if any velocity or acceleration constraint(s) is still violated, the time points are scaled, thereby increasing the total motion time, and the procedure is iterated.

The same method can be used if B is increased or reduced in magnitude only, but in that case, the intermediate target field vectors can be interpolated directly with no need for a polynomial fit.

Part C): Inverse Method

Figure 8:
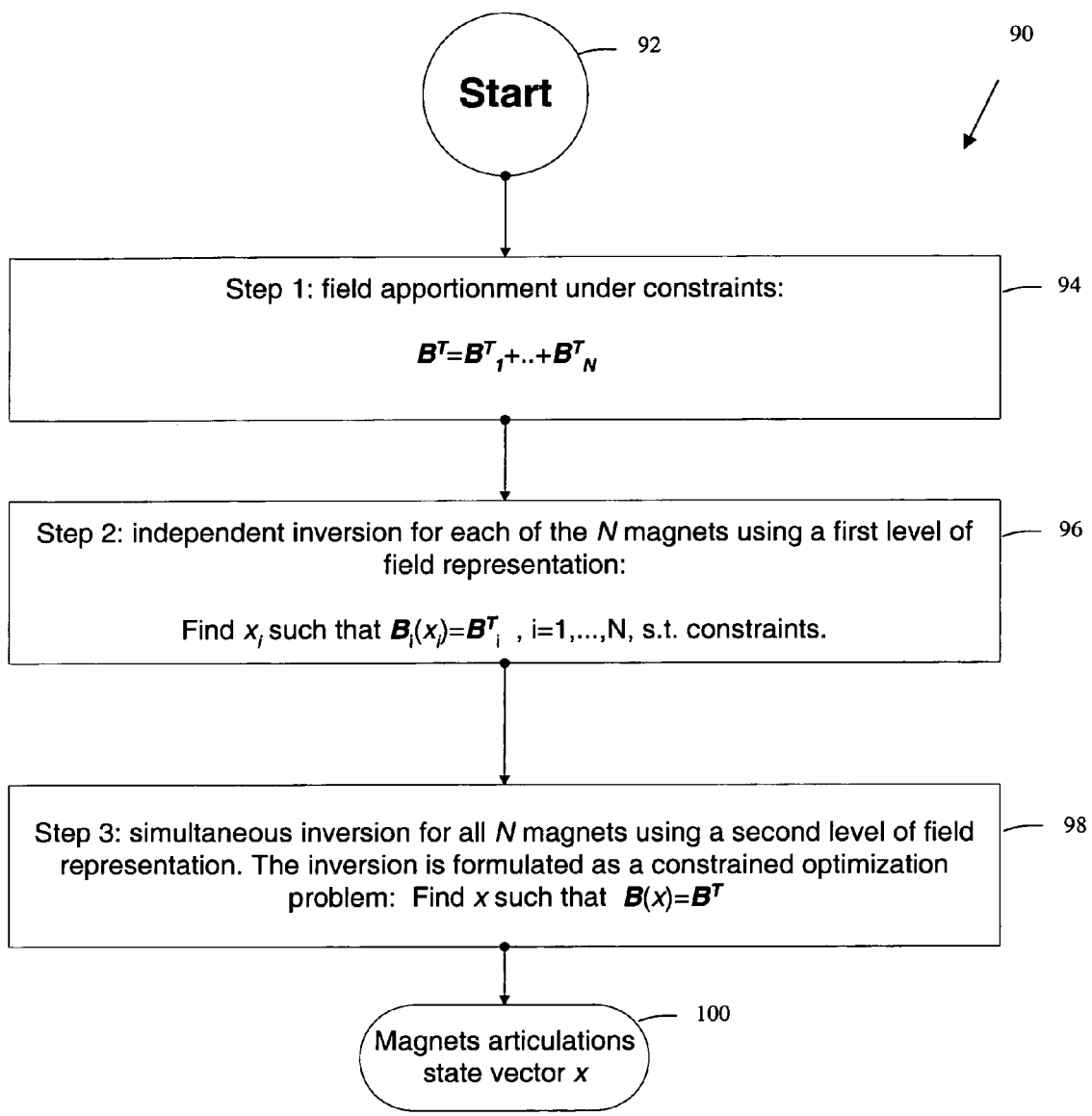
FIG. 8 presents the three-step inversion algorithm flowchart.

The inverse algorithm proceeds in three steps, further described below, and illustrated in the flowchart 90 of FIG. 8. In the first step 94, the target magnetic field magnitude $b=|B^T|$ is apportioned between the multiple magnets. In one embodiment, the field magnitude b is apportioned between two magnets: $b=b_1+b_2$. Two methods are described for this apportionment, a geometric method, and an optimization method that also enables consideration of specific constraints via the inclusion of corresponding cost function terms. In the second step 96, first the initial rotation and pivoting are performed to i) align the desired $B_i^T$ vector in the $X^M$, $Z^M$ plane and ii) to put the operating point on the $Z^M$ axis in order to determine the magnitude bounds for each magnet. Then, using the nested polynomial field magnitude and angle representations described above in Part A), the pivoting angle and corresponding Z translation (if necessary) are found that solve the field problem for each magnet independently. In the third step 98, the more accurate field representation using spherical harmonic representation is used to solve the problem formulated as a simultaneous optimization in all magnet coordinates and obtain an improved solution 100 that more closely match the target magnetic field in angle and magnitude.

Part C), Step One: Field Apportionment

This section details the geometric field magnitude allocation method. This method provides an apportionment of $b=|B^T|$ to $b_1$, $b_2$ (and therefore, as will be seen below, of $B^T$ to $B_1$ and $B_2$) by considering the magnitude bounds for each magnet. During navigation, and to maintain field strength, the two fields contribute constructively (additively, i.e., with both fields in the direction of the desired vector). In the procedure known as field reduction (not performed during navigation of a medical device in a subject), the fields contribute destructively (i.e., with the two fields in opposite directions).

For any particular target field, it is necessary to find whether the proposed apportioned fields are within the upper and lower bounds of each magnet. Different situations are illustrated in FIGS. 9-A through 9-C, all showing plots of the dashed line $b_1=b_2$ 112 and the solid line $b=b_1+b_2$ 114 with respect to the axes $b_1$ 116 and $b_2$ 118. The lower and upper bounds of the respective magnet fields $B_1^M$ and $B_2^M$ are indicated by $t_1$, 120, $u_1$, 122, $l_2$, 124, and $u_2$, 126. Intersection of the dashed line $b_1=b_2$ and the solid line $b=b_1+b_2$ provide appropriate categorization. If b/2 is within the bounds of $B_1^M$ and $B_2^M$, then $b_1=b_2=b/2$. This case is illustrated in 9-A, 130, where the intersection of the two lines occurs within the rectangle 132 representing the magnet bounds. As described previously, this is a most favorable condition, as it minimizes the magnetic field gradient. For some field directions and some locations within the navigation volume, these bounds will not be met. FIGS. 9-B and 9-C show two cases for which the line crossings fall outside the rectangle formed by the magnets bounds. In such cases the apportionment is determined as follows: Take the intersection of the rectangular region of valid magnitudes with the line $b=b_1+b_2$. If this intersection is empty, then select the vertex of the rectangle closest to the line. If the intersection is non-empty, then find on this intersection the point closest to the crossing of the two lines $b=b_1+b_2$ and $b_1=b_2$. In FIG. 9-B, 140, the lines intersect at point $A=(A_1, A_2)$, 142, and the closest bound is at $A'=(A'_1, A'_2)$, 144. Thus $b_1=l_1=A'_1$, 120, and $b_2=A'_2$, 148, are the retained apportionments. In the case of FIG. 9-C, 150, the lines cross at C, 152, and the closest valid point is $C'=(C'_1, C'_2)$, 154, so the corresponding apportionments are $b_1=u_1=C'_1$, 122, and $b_2=C'_2$, 158.

This section details the penalized optimization field magnitude allocation method. The problem is formulated as a constrained optimization problem. There are six variables, consisting of the three field components for each of the two magnets. There are three equality constraints from the equation $B_1+B_2=B$. In addition there are four inequality constraints from the bounds $l_1 \leq b_1 \leq u_1$ and $l_2 \leq b_2 \leq u_2$. The components of the cost functions are chosen as follows:

1) $|b_1-b_2|^2$, to reduce the field gradient;

2) $[B_{1,z}/b_1]^2+[B_{2,z}/b_2]^2$, to reduce the fields components along the coordinate axis perpendicular to the magnet surface; this constraint minimizes the amount of pivoting required;

3) $b_1^2+b_2^2$, to force the fields to add constructively.

The respective terms of the cost functions are combined by weights determined by experience. The problem is solved in closed-form using Lagrange multipliers. A solution can always be found, considering the small number of constraint surfaces. There is a sufficiently small number of Kuhn-Tucker points (stationary points of the Lagrangian) that each satisfies first-order necessary conditions for a (local) minimum, that they can all be checked and compared in turn to determine the global minimum. A general expression for the Lagrangian is:

$$L(x,\lambda,\mu)=f(x)+\lambda^T g(x)+\mu^T h(x),$$

where g(x) represents equality conditions and h(x) represents inequality conditions.

In this section, the problem of apportioning a target magnetic field $B^T$ to N magnets is considered:

$$B^T = \sum_{i=1}^{i=N} B_i$$

The geometric apportionment method for N=2 extends to the general case in a straightforward manner. As before, select the field direction for each magnet the same as $B^T$. In order to apportion the magnitudes, define the hyperplane $$H = \left\{\sum_{i=1}^{i=N} b_i = b\right\},$$

the line L={$b_i=b_j$, $i,j,=1,\ldots,N$}, the rectangular polyhedron R={$l_i \leq b_i \leq u_i$}, and the point d=H∩L, L={$b_i=b/N$ i=1, ..., N}. If the intersection of H and R is empty, meaning that there is no valid selection of individual field magnitudes that add up to the target magnitude, then select the vertex of R closest to H in Euclidean norm as the apportionment point. Since none of the edges of R can be parallel to H, this vertex is unique. If the intersection of H and R is nonempty, then it will define a polytope P of dimension N−1. The apportionment point is selected as the point in P closest to d in Euclidean norm. Since P is a closed convex set, this point is unique. Computationally this point can be found by solving the following linear least-squares problem:

$$\min\{\|y-d\|^2, y \in P\}$$

and setting $b_i=y_i$. Since this is a quadratic program with linear equality and inequality constraints, it can be solved efficiently using the algorithm described in below.

Alternatively, the optimization field magnitude allocation method of above can be generalized for N magnets as follows: There are 3N variables, consisting of the three field components of the N magnets. There are three equality constraints from the equation $$\sum_{i=1}^{i=N} B_i = B^T.$$

In addition there are 2N inequality constraints from the bounds $l_i \leq b_i \leq u_i$ $i=1, \ldots, N$. The components of the cost functions are chosen as follows:

1) $\sum_{i=1}^{i=1} |b_i - b/N|^2,$ to reduce the field gradient;

2) $\sum_{i=1}^{i=N} (B_{z,i}/\|B_i\|)^2,$ to reduce the fields components along the world coordinate axis perpendicular to the magnet surface; this constraint minimizes the amount of pivoting required;

3) $\sum_{i=1}^{i=N} b_i^2,$ to force the fields to add constructively. This can be solved using an iterative algorithm for constrained nonlinear programming.

Part C), Step 2: Independent Magnet Control using Polynomial Field Representations In the previous step, the field apportionment of b to $b_1$ and $b_2$ and thus of $B^T$ to $B_1$ and $B_2$ was found. The problem solved in this section is to that of finding the state sub-vector $x_1$ that yield $B_1$ at the operating point. This step is carried out independently for each magnet using a first order magnet field representation.

First, the rotation angle $\theta_1$ is found such that $B_1$ is contained in an $(X^M, Z^M)$ magnet $M_1$ plane. This is achieved by projecting $B_1$ onto the $(X^M, Y^M)$ plane. The angle $-\theta_1$ is then the angle between $-X^M$ and the projection of $B_1$.

Second, the pivoting angle $\phi_1$ is found that aligns the magnet $Z^M$ axis with the line from the magnet coordinate center to the operating point, i.e. brings the operating point to the $(Y^M, Z^M)$ plane. At this stage, the field magnitude bounds are determined.

The vector $B_1$ now lies in an $(X^M, Z^M)$ magnet plane; $B_1$ forms a known angle $\beta_1$ with the $-X^M$ axis.

The next step is then to determine the combination of variables ($\phi_1$, $Z_1$) that will provide a field matching $B_1$ at the operating point. This can be achieved in two ways:

i) By performing bisection searches using a look-up table field representation of the field (knowing that both the field magnitude and the field angle are monotonic functions of the distance p and of the pivoting angle $\phi$). The use of such look-up tables requires time-consuming three-dimensional interpolations; or:

ii) In a preferred embodiment, by using the nested-polynomial field representation previously introduced. In this approximation, the magnet field component along $Y^M$ is ignored. First the pivoting angle $\alpha_1$ is estimated by plugging $\beta_1$ into the functional $\alpha(\beta)$ and then the distance $\rho$ is found by inverting the quadratic form for $1/b$. In this way, the target position that gives the desired field $B_1$ is found in the magnet frame using cylindrical coordinates. Finally, the magnet translation Z (function of $\rho$) and pivoting angle $\phi$ (function of $\alpha$) are found from the system geometry and corresponding motions are implemented to bring the actual target point to the desired target position.

Part C), Step 3: Constrained Simultaneous Optimization using a more Accurate Field Representation In step 3, the problem of finding a state vector x that yields a total contributed field B(x) equal to the target field $B^T$ at the operating point is formulated as a penalized optimization problem by considering the multiple magnets simultaneously and by using a more accurate spherical harmonics field representation. This step will in general improve upon the solution found in step 2 and provide an optimized solution that more closely match the target magnetic field in angle and magnitude.

As a result of step 2, a state vector estimate x is available; that estimate was derived from independent inversion for each of the magnets using nested-polynomial field representations. The algorithm now proceeds to find a state vector x (for all magnets) that minimizes the Euclidian distance between the target and the estimated fields $|B^T - B(x)|^2$, using a more accurate field representation. There are potentially an infinite number of solutions. The Euclidian distance cost function may have a long shallow valley, for which convergence is difficult in at least one dimension. The following constraints regularize the problem and allow quick convergence to an optimum. First, a component is added to the cost function to minimize the distance to the solution of step 2 (with a small weight). Adding this term cups the end of the valleys, making the cost function locally convex and improving the likelihood of finding a unique solution. Another, independent non-linear constraint is to avoid interference of the stationary covers with the moving magnets. This might require that as the magnet pivots, the magnet be pulled back in Z. This constraint is shown in FIG. 4. The pivoting angle is also limited to the range: $-40° < \phi < 40°$, and $Z > -4"$. The rotation angle is not constrained. This optimization problem is a nonlinear least-squares problem with upper and lower bounds on the variables and the nonlinear constraints due to the covers. The problem is formulated as a penalized optimization problem, and the total cost function can be written as the summation of squares of nonlinear functions $f_i(x)$. This problem is solved by the following iterative procedure.

At each step, the cover-related nonlinear constraints are locally approximated with linear chords of the $Z(\phi)$ curves as exemplified in FIG. 4. The chord is chosen around the current point, in a range that depends on whether the curve is locally concave or convex. If during algorithm iterations the cover constraint is slightly violated due to the chord approximation, the Z variable is adjusted to meet the constraint. Each term $f_i$ squared in the cost function is approximated by its linear term, thus resulting in a quadratic sub-optimization problem for this step. A search direction (also known as the Gauss-Newton direction) d is selected from the linear manifold of active constraints. Along this direction, a line search using quadratic polynomial fit approximation to the non-linear total cost function is performed that yields a local minimum and the next state vector iterate. At the end of the step, a new constraint may become active, an formerly active constraint may have become inactive, or a global minimum point is reached, which is then the solution of the main optimization problem.

This algorithm has been tested by computer simulations for 30,000 points in the subject operation volume, in which the target field magnitude was 0.1 Tesla. Step 2 yields angle errors of less than 1.7 degrees in 95% of the samples, with a maximum of 11 degrees. In comparison, step 3 reduces the angle errors to less than 0.73 degrees in 95% of the samples, with a maximum of 2.9 degrees. For magnitude errors, step 2 yields less than 5.3 mTesla in 95% of the samples with a maximum of 9.4 mTesla. In comparison, step 3 reduces the magnitude errors to less than 4.3 mTesla in 95% of the samples, with a maximum of 8.4 mTesla. Histograms of these results are shown in FIGS. 10-A and 10-B for step 2 and FIGS. 11-A and 11-B for step 3. On average, steps 1 and 2 together take 3 ms, and step 3 takes 140 ms on a personal computer.

The extension of the methods of steps 2 and 3, described in sections [0050]-[0055] to more than two magnets (N≧3) is straightforward. Since step 2 is carried out for each magnet independently, it applies without modification. In step 3, the same cost function and constraints can be written in a space of dimension 3N, and the iterative solution procedure described above will find the solution, although it will take more computation time to perform.

Quasi-Continuous Navigation

In one embodiment of the algorithm, a target field $B^T$ is generated by the operator using an input device such as a joystick. At the same time, the operating point may remain fixed, or it may also be changed by the operator using another input device, such as a pointing device, or it may be automatically calculated by the system using a mechanical model of the interventional device being navigated. A new target field or a new operating point may be requested while the magnets are moving, along the trajectory calculated by the algorithm, corresponding to the previously requested field. In this case, the algorithm is modified as follows: The magnets are decelerated to stop at an intermediate position; during the deceleration, the path calculation is repeated, this time starting from the intermediate position and ending at the position corresponding to the newly requested target field; and the motion is started again. This may be repeated as often as necessary, whenever a new field request is generated by the operator, implementing a version of quasi-continuous navigation.

Haptic Feedback

During quasi-continuous navigation, it is useful to provide haptic feedback to the operator by applying a resistive force to the joystick. The force will indicate the subjective difficulty of the requested field change. The difficulty may be represented by making the resistive force proportional to either one of the following alternatives, or a combination of these:

i. The weighted sum of the difference between the current and the final joint positions, i.e. the distance traveled by each joint.

ii. The estimated time required to reach the final joint state. The time may be calculated as the maximum of the required times for each joint using the distance traveled and a parabolic velocity profile; or it may be calculated using the path generation algorithm in Part B.

iii. The vector difference between the current and final field vectors. This would provide a directional resistive force.

More Degrees of Freedom—Secondary Mechanism

More degrees of freedom may be added, by using a secondary articulation mechanism, in order to move each magnet together with its primary articulation mechanism, so as to obtain a better imaging angle or for patient access etc. The secondary mechanism may be floor- or ceiling-mounted, and may be constructed independent of the primary mechanism. During the motion of the secondary mechanism, the relationship between each magnet and its primary articulation mechanism remains the same, so that all the calculations described before for the three axes of motion, Z, θ and φ apply without modification. However, the relationship between each magnet and the patient changes. Therefore, it is desirable to coordinate the motions of the primary and the secondary mechanisms so that the generated field B remains the same in the patient. This may be accomplished by modifying the algorithm as follows: First intermediate points are selected along the motion trajectory for the axes of the secondary mechanism. At each intermediate time point, the transformation between the patient and each magnet frame is recalculated. Next, at each intermediate point, Part C Steps 1 and 2 are repeated for each magnet to find the corresponding joint positions of the primary mechanism to generate the target field. At the final time, Part C Step 3 is performed combining all magnets. Finally, Part B is performed separately for each magnet to determine the motion trajectory.

In one embodiment, the secondary mechanism performs a tilting motion that rotates each magnet and its primary mechanism around the imaging isocenter without changing the relationship between the magnet frames.

Feedback from a Magnetic Sensor

If it is desired to improve the accuracy of the generated magnetic field beyond the accuracy of the numerical representation in Part A, then one may use a high precision magnetic field sensor to measure the actual field vector $B^m$ at the operating point. First, the navigation algorithm described in Parts B and C is performed to bring the magnets to a penultimate joint position x, with the corresponding measured field $B^m(x)$. Let $e(x)=B^T-B^m(x)$ be the vector error between the target and measured fields. Denote the derivative of the field with respect to the joint state vector x by $A(x)=\partial B(x)/\partial x$. Corresponding to a small increment v in the joint position vector, the linear approximation of the field around the penultimate position x is $B(x+v)\approx B(x)+A(x) v$. The increment is calculated as the minimizer of the cost function $$\|A v-e\|^2+v^T R v$$

where R is a diagonal matrix with positive entries chosen by experience as weights to penalize large changes in the corresponding joint variable. Since the matrix R is positive definite, the unique increment v is found by solving the linear system $$(A^T A+R)v=A^T e=A^T(B^T-B^m)$$

which constitutes a feedback law using the magnetic sensor. Then, the increment in the Z positions of the magnets are modified if necessary to satisfy the cover constraint in Part B. The time required to perform this increment is determined as the shortest time that satisfies the velocity and acceleration constraints in Part B.

If, after such an increment, the magnitude of error in the field vector is larger than a specified value, then the increment procedure is repeated starting from the modified joint vector x+v, until the error is small enough or a given maximum number of iterations is reached The advantages of the above described embodiment and improvements should be readily apparent to one skilled in the art. Accordingly, it is not intended that the invention be limited by the particular embodiment or form described above, but by the appended claims.

What is claimed is:

1. A method of determining the positions and orientations of at least two magnets to apply a magnetic field at an operating point of specified strength and direction, the method comprising:
   (1) apportioning the contribution to the desired field of each of the at least two magnets;
   (2) individually determining for each of the at least two magnets, a position and orientation to achieve the apportioned contribution using a representation of the magnetic field of each the magnet;
   (3) simultaneously determining a position and orientation of each of the at least two magnets two magnets to achieve the desired field, using the individually determined positions and orientations and a representation of the magnetic field of each magnet.

2. The method of claim 1 wherein the representations of the magnetic field used in step (3) are different from the representations of the magnetic field used in step (2).

3. The method of claim 1 wherein step (2) comprises using a nested polynomial representation of the field of each magnet.

4. The method of claim 1 wherein step (3) comprises using a spherical harmonics expansion field representation of the field of each magnet.

5. The method of claim 1 wherein step (3) is performed as a simultaneous optimization of all degrees of freedom.

6. A method of generating a specific target magnetic field at an operating point in space, the method comprising the steps of:
   (a) representing magnet and application related constraints;
   (b) defining a series of intermediate field vectors at the operating point;
   (c) using an inversion method to find a series of method control parameters for a multiplicity of magnets associated with the series of field vectors of step (b);
   (d) finding a time sequence of control parameters for the multiplicity of magnets of step (c) subject to the constraints of step (a) to approximate the series of control parameters of step (c); and
   (e) performing the time sequence of step (d),
      whereby the target magnetic field at the operating point is achieved at a given level of accuracy and within a specific time interval.

7. The method of claim 6, wherein the series of intermediate field vectors at the operating point lie in the plane formed by the initial and the target magnetic field vectors at the operating point.

8. The method of claim 6, wherein the time sequence is obtained by fitting the series of magnets control parameters of step (c) by representing the distance between the fit functions and the series as one of the Lagrangian terms.

9. A method of representing the magnetic field generated by a magnet, the method comprising the steps of:
   (a) providing a least a first level of magnetic field representation such that the magnet control parameters that will provide a specific magnetic field generated by the magnet at an operating point in space within a first level of accuracy can be found efficiently; and
   (b) providing at least a second level of magnetic field representation such that the magnet control parameters that will provide a specific magnetic field generated by a multiplicity of magnets at an operating point in space at a second, higher, level of accuracy can be found efficiently; and
   (c) designing the magnetic field representations of steps (a) and (b) such that the control parameters found by using the representations provided in step (a) for the multiplicity of magnets under consideration in step (b) will provide an initial point in the neighborhood of the final solution for the procedure of finding the control parameters using the representation provided in step (b);
      whereby the control parameters for a multiplicity of magnets that will generate a specific magnetic field at an operating point in space within a second, higher level of accuracy subject to design and application related constraints can be found efficiently.

10. The method of claim 9, wherein the step (a) of providing at least a first level of magnetic field representation comprises the use of nested polynomials.

11. The method of claim 10, wherein the nested polynomials provide a one-to-one correspondence between a couple consisting of a magnetic field magnitude and magnetic field orientation within a magnet plane of constant coordinate $Y^m$ and a triplet of magnet articulations consisting of a rotation angle $\theta$, a pivoting angle $\Phi$, and a translation distance Z.

12. The method of claim 9, wherein the step (b) of providing a second level of magnetic field representation comprises using a spherical harmonics function expansion, and calculating the expansion coefficients for optimal accuracy given a number of expansion terms by minimizing the representation error in a local volume; said local volume always containing the operating point.

13. The method of claim 1 wherein the apportioning comprises distributing a target magnetic field at an operating point in space among the at least two magnets subject to design and application related constraints, whereby the sum of the magnetic fields contributed by the at least two magnets at the operating point is equal to the target magnetic field at the operating point.

14. The method of claim 13, further constraining the fields generated by each controlled magnet to be aligned with the target magnetic field and such that the target field magnitude is distributed in equal parts to all controlled magnets.

15. The method of claim 14, where adjustments are made to the field apportionments to account for each magnet lower and upper field magnitudes at the operating point.

16. The method of claim 6, wherein the inversion method comprises the steps of:
   (a) using a magnetic field representation;
   (b) representing magnet design and application related constraints;
   (c) finding the magnet control parameters using the representation of step (a) and under the constraints of step (b) that will provide a magnetic field at an operating point in space,
      whereby a target magnetic field at the operating point in space is obtained at a given level of accuracy.

17. The inversion method of claim 16, using a nested polynomial magnetic field representation and further comprising the steps of:
   (a) pivoting the magnet by an angle $\Phi$ such that the operating point lies on the $Z^m$ magnet axis and with a plane of constant $Y^m$;
   (b) calculating the rotation angle $\theta$ such that the apportioned target magnetic field lies in a plane of constant $Y^m$ in the magnet under consideration;

(c) calculating the target magnetic field angle $\beta$ with respect to the Magnet—$X^m$ axis;

(d) calculating the cylindrical coordinate angle $\alpha$ of a point within the magnet such that the associated magnetic field generated by the magnet lies at an angle $\alpha+\beta$ with respect to magnet axis—$X^m$;

(e) calculating the cylindrical coordinate $\rho$ of a point within the magnet at an angle $\alpha+\beta$ such that the magnet field magnitude at that point equals that of the apportioned field;

(f) calculating from planar geometry the magnet translation Z and pivoting $\phi$ that will bring the target point to the desired position within the magnet for generation of the apportioned field at the operating point; and (g) carrying out the rotation of angle $\theta$, pivoting of angle $\phi$, and translation along $Z^m$ to bring the target point to the desired point within the magnet.

18. The inversion method of claim 16, using a spherical harmonics expansion representation for the magnetic field of each magnet and further comprising the step of formulating the problem as a non-linear constrained optimization method.

19. The inverse method of claim 18, further comprising the steps of:

(a) at each algorithm iteration, locally modeling non-linear cost functions via their linear approximations and including the square of the linear terms in a sub-problem optimization cost function;

(b) adding a quadratic term to the cost function that varies according to the square of the distance between the current iteration state vector x and the initial optimization state vector $x_0$;

(c) solving at each iteration step the local quadratic sub-problem using known techniques of constrained optimization; and (d) iterating on steps (a) through (c) above till a solution to the initial optimization problem has been reached.

20. The method of claim 6, wherein the inversion method for the multiplicity of magnets comprises the steps of:

(a) using a multiplicity of magnetic field representations for each the magnets;

(b) representing magnet design and application related constraints;

(c) using a first inversion method in a first stage to find the magnets control parameters using a first level of magnetic field representation of step (a) and under the constraints of step (b) that will provide a magnetic field at an operating point in space at a first level of accuracy;

(d) using a second inversion method in a second stage, the magnet control parameters of step (c) as a starting point, and a second level of magnetic field representation of step (a), finding under the constraints of step (b) the magnet control parameters that will provide a magnetic field at the operating point in space at a second, higher, level accuracy, whereby the target magnetic field at the operating point in space is achieved at a high level of accuracy and within a specified time interval by the multiplicity of magnets under control.

* * * * *